US012616518B2

(12) United States Patent
Okarski et al.

(10) Patent No.: US 12,616,518 B2
(45) Date of Patent: May 5, 2026

(54) BARREL ELECTRODES FOR A BASKET CATHETER, AND METHODS OF THE SAME

(71) Applicant: Biosense Webster (Israel) Ltd., Yokneam (IL)

(72) Inventors: Kevin Mark Okarski, Monrovia, CA (US); Thanh Nguyen, El Monte, CA (US); Abubakarr Bah, Irvine, CA (US); Keshava Datta, Chino Hills, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 504 days.

(21) Appl. No.: 18/185,313

(22) Filed: Mar. 16, 2023

(65) Prior Publication Data

US 2023/0346463 A1     Nov. 2, 2023

Related U.S. Application Data

(60) Provisional application No. 63/336,072, filed on Apr. 28, 2022.

(51) Int. Cl.
| | |
|---|---|
| *A61B 18/14* | (2006.01) |
| *A61B 17/00* | (2006.01) |
| *A61B 18/00* | (2006.01) |

(52) U.S. Cl.
CPC ..................... *A61B 18/1492* (2013.01); *A61B 2017/00526* (2013.01); *A61B 2018/00029* (2013.01); *A61B 2018/0016* (2013.01); *A61B 2018/00267* (2013.01); *A61B 2018/1405* (2013.01); *A61B 2018/1467* (2013.01)

(58) Field of Classification Search
CPC .. A61B 2018/0016; A61B 2018/00267; A61B 5/6858; A61B 2018/1405
See application file for complete search history.

(56) References Cited

U.S. PATENT DOCUMENTS

| | | | |
|---|---|---|---|
| 4,699,147 | A | 10/1987 | Chilson et al. |
| 4,940,064 | A | 7/1990 | Desai |
| 5,215,103 | A | 6/1993 | Desai |
| 5,255,679 | A | 10/1993 | Imran |
| 5,293,869 | A | 3/1994 | Edwards et al. |
| 5,309,910 | A | 5/1994 | Edwards et al. |
| 5,313,943 | A | 5/1994 | Houser et al. |

(Continued)

FOREIGN PATENT DOCUMENTS

| | | |
|---|---|---|
| CN | 111248993 A | 6/2020 |
| CN | 111248996 A | 6/2020 |

(Continued)

OTHER PUBLICATIONS

Extended European Search Report and Search Opinion dated Sep. 21, 2023, from corresponding European Application No. 23170400.8.

*Primary Examiner* — Jaymi E Della

(57) ABSTRACT

The disclosed technology includes an electrode for a medical probe having an elongated body. At least a portion of the elongated body can be electrically conductive. The elongated body can define a lumen that extends through the elongated body along a longitudinal axis of the elongated body. The electrode can include a locking stub that extends at least partially into the lumen so that the locking stub is locked to a member inserted into the lumen.

10 Claims, 8 Drawing Sheets

(56)                    References Cited

U.S. PATENT DOCUMENTS

| | | | |
|---|---|---|---|
| 5,324,284 A | 6/1994 | Imran | |
| 5,345,936 A | 9/1994 | Pomeranz et al. | |
| 5,365,926 A | 11/1994 | Desai | |
| 5,396,887 A | 3/1995 | Imran | |
| 5,400,783 A | 3/1995 | Pomeranz et al. | |
| 5,411,025 A | 5/1995 | Webster, Jr. | |
| 5,415,166 A | 5/1995 | Imran | |
| 5,456,254 A | 10/1995 | Pietroski et al. | |
| 5,465,717 A | 11/1995 | Imran et al. | |
| 5,476,495 A | 12/1995 | Kordis et al. | |
| 5,499,981 A | 3/1996 | Kordis | |
| 5,526,810 A | 6/1996 | Wang | |
| 5,546,940 A | 8/1996 | Panescu et al. | |
| 5,549,108 A | 8/1996 | Edwards et al. | |
| 5,558,073 A | 9/1996 | Pomeranz et al. | |
| 5,577,509 A | 11/1996 | Panescu et al. | |
| 5,595,183 A | 1/1997 | Swanson et al. | |
| 5,598,848 A | 2/1997 | Swanson et al. | |
| 5,609,157 A | 3/1997 | Panescu et al. | |
| 5,628,313 A | 5/1997 | Webster, Jr. | |
| 5,681,280 A | 10/1997 | Rusk et al. | |
| 5,722,401 A | 3/1998 | Pietroski et al. | |
| 5,722,403 A | 3/1998 | McGee et al. | |
| 5,725,525 A | 3/1998 | Kordis | |
| 5,730,128 A | 3/1998 | Pomeranz et al. | |
| 5,772,590 A | 6/1998 | Webster, Jr. | |
| 5,782,899 A | 7/1998 | Imran | |
| 5,823,189 A | 10/1998 | Kordis | |
| 5,881,727 A | 3/1999 | Edwards | |
| 5,893,847 A | 4/1999 | Kordis | |
| 5,904,680 A | 5/1999 | Kordis et al. | |
| 5,911,739 A | 6/1999 | Kordis et al. | |
| 5,928,228 A | 7/1999 | Kordis et al. | |
| 5,968,040 A | 10/1999 | Swanson et al. | |
| 6,014,579 A | 1/2000 | Pomeranz et al. | |
| 6,014,590 A | 1/2000 | Whayne et al. | |
| 6,119,030 A | 9/2000 | Morency | |
| 6,178,354 B1 * | 1/2001 | Gibson | A61B 18/1492 |
| | | | 607/116 |
| 6,216,043 B1 | 4/2001 | Swanson et al. | |
| 6,216,044 B1 | 4/2001 | Kordis | |
| 6,428,537 B1 | 8/2002 | Swanson et al. | |
| 6,456,864 B1 | 9/2002 | Swanson et al. | |
| 6,574,492 B1 | 6/2003 | Ben-Haim et al. | |
| 6,584,345 B2 | 6/2003 | Govari | |
| 6,600,948 B2 | 7/2003 | Ben-Haim et al. | |
| 6,738,655 B1 | 5/2004 | Sen et al. | |
| 6,741,878 B2 | 5/2004 | Fuimaono et al. | |
| 6,748,255 B2 | 6/2004 | Fuimaono et al. | |
| 6,780,183 B2 | 8/2004 | Jimenez, Jr. et al. | |
| 6,837,886 B2 | 1/2005 | Collins et al. | |
| 6,866,662 B2 | 3/2005 | Fuimaono et al. | |
| 6,892,091 B1 | 5/2005 | Ben-Haim et al. | |
| 6,970,730 B2 | 11/2005 | Fuimaono et al. | |
| 6,973,340 B2 | 12/2005 | Fuimaono et al. | |
| 6,980,858 B2 | 12/2005 | Fuimaono et al. | |
| 7,048,734 B1 | 5/2006 | Fleischman et al. | |
| 7,149,563 B2 | 12/2006 | Fuimaono et al. | |
| 7,255,695 B2 | 8/2007 | Falwell et al. | |
| 7,257,434 B2 | 8/2007 | Fuimaono et al. | |
| 7,399,299 B2 | 7/2008 | Daniel et al. | |
| 7,410,486 B2 | 8/2008 | Fuimaono et al. | |
| 7,522,950 B2 | 4/2009 | Fuimaono et al. | |
| RE41,334 E | 5/2010 | Beatty et al. | |
| 7,846,157 B2 | 12/2010 | Kozel | |
| 7,930,018 B2 | 4/2011 | Harlev et al. | |
| 8,007,495 B2 | 8/2011 | McDaniel et al. | |
| 8,048,063 B2 | 11/2011 | Aeby et al. | |
| 8,103,327 B2 | 1/2012 | Harlev et al. | |
| 8,167,845 B2 | 5/2012 | Wang et al. | |
| 8,224,416 B2 | 7/2012 | De La Rama et al. | |
| 8,235,988 B2 | 8/2012 | Davis et al. | |
| 8,346,339 B2 | 1/2013 | Kordis et al. | |
| 8,435,232 B2 | 5/2013 | Aeby et al. | |
| 8,447,377 B2 | 5/2013 | Harlev et al. | |

| | | | |
|---|---|---|---|
| 8,498,686 B2 | 7/2013 | Grunewald | |
| 8,517,999 B2 | 8/2013 | Pappone et al. | |
| 8,545,490 B2 | 10/2013 | Mihajlovic et al. | |
| 8,560,086 B2 | 10/2013 | Just et al. | |
| 8,567,265 B2 | 10/2013 | Aeby et al. | |
| 8,712,550 B2 | 4/2014 | Grunewald | |
| 8,755,861 B2 | 6/2014 | Harlev et al. | |
| 8,825,130 B2 | 9/2014 | Just et al. | |
| 8,906,011 B2 | 12/2014 | Gelbart et al. | |
| 8,945,120 B2 | 2/2015 | McDaniel et al. | |
| 8,979,839 B2 | 3/2015 | De La Rama et al. | |
| 9,037,264 B2 | 5/2015 | Just et al. | |
| 9,131,980 B2 | 9/2015 | Bloom | |
| 9,204,929 B2 | 12/2015 | Solis | |
| 9,277,960 B2 | 3/2016 | Weinkam et al. | |
| 9,314,208 B1 | 4/2016 | Altmann et al. | |
| 9,339,331 B2 | 5/2016 | Tegg et al. | |
| 9,486,282 B2 | 11/2016 | Solis | |
| 9,554,718 B2 | 1/2017 | Bar-Tal et al. | |
| D782,686 S | 3/2017 | Werneth et al. | |
| 9,585,588 B2 | 3/2017 | Marecki et al. | |
| 9,597,036 B2 | 3/2017 | Aeby et al. | |
| 9,687,297 B2 | 6/2017 | Just et al. | |
| 9,693,733 B2 | 7/2017 | Altmann et al. | |
| 9,782,099 B2 | 10/2017 | Williams et al. | |
| 9,788,895 B2 | 10/2017 | Solis | |
| 9,801,681 B2 | 10/2017 | Laske et al. | |
| 9,814,618 B2 | 11/2017 | Nguyen et al. | |
| 9,833,161 B2 | 12/2017 | Govari | |
| 9,894,756 B2 | 2/2018 | Weinkam et al. | |
| 9,895,073 B2 | 2/2018 | Solis | |
| 9,907,609 B2 | 3/2018 | Cao et al. | |
| 9,974,460 B2 | 5/2018 | Wu et al. | |
| 9,986,949 B2 | 6/2018 | Govari et al. | |
| 9,993,160 B2 | 6/2018 | Salvestro et al. | |
| 10,014,607 B1 | 7/2018 | Govari et al. | |
| 10,028,376 B2 | 7/2018 | Weinkam et al. | |
| 10,034,637 B2 | 7/2018 | Harlev et al. | |
| 10,039,494 B2 | 8/2018 | Altmann et al. | |
| 10,045,707 B2 | 8/2018 | Govari | |
| 10,078,713 B2 | 9/2018 | Auerbach et al. | |
| 10,111,623 B2 | 10/2018 | Jung et al. | |
| 10,130,420 B2 | 11/2018 | Basu et al. | |
| 10,136,828 B2 | 11/2018 | Houben et al. | |
| 10,143,394 B2 | 12/2018 | Solis | |
| 10,172,536 B2 | 1/2019 | Maskara et al. | |
| 10,182,762 B2 | 1/2019 | Just et al. | |
| 10,194,818 B2 | 2/2019 | Williams et al. | |
| 10,201,311 B2 | 2/2019 | Chou et al. | |
| 10,219,860 B2 | 3/2019 | Harlev et al. | |
| 10,219,861 B2 | 3/2019 | Just et al. | |
| 10,231,328 B2 | 3/2019 | Weinkam et al. | |
| 10,238,309 B2 | 3/2019 | Bar-Tal et al. | |
| 10,278,590 B2 | 5/2019 | Salvestro et al. | |
| D851,774 S | 6/2019 | Werneth et al. | |
| 10,314,505 B2 | 6/2019 | Williams et al. | |
| 10,314,507 B2 | 6/2019 | Govari et al. | |
| 10,314,648 B2 | 6/2019 | Ge et al. | |
| 10,314,649 B2 | 6/2019 | Bakos et al. | |
| 10,349,855 B2 | 7/2019 | Zeidan et al. | |
| 10,350,003 B2 | 7/2019 | Weinkam et al. | |
| 10,362,991 B2 | 7/2019 | Tran et al. | |
| 10,375,827 B2 | 8/2019 | Weinkam et al. | |
| 10,376,170 B2 | 8/2019 | Quinn et al. | |
| 10,376,221 B2 | 8/2019 | Iyun et al. | |
| 10,398,348 B2 | 9/2019 | Osadchy et al. | |
| 10,403,053 B2 | 9/2019 | Katz et al. | |
| 10,441,188 B2 | 10/2019 | Katz et al. | |
| 10,470,682 B2 | 11/2019 | Deno et al. | |
| 10,470,714 B2 | 11/2019 | Altmann et al. | |
| 10,482,198 B2 | 11/2019 | Auerbach et al. | |
| 10,492,857 B2 | 12/2019 | Guggenberger et al. | |
| 10,542,620 B2 | 1/2020 | Weinkam et al. | |
| 10,575,743 B2 | 3/2020 | Basu et al. | |
| 10,575,745 B2 | 3/2020 | Solis | |
| 10,582,871 B2 | 3/2020 | Williams et al. | |
| 10,582,894 B2 | 3/2020 | Ben Zrihem et al. | |
| 10,596,346 B2 | 3/2020 | Aeby et al. | |
| 10,602,947 B2 | 3/2020 | Govari et al. | |

(56) References Cited

U.S. PATENT DOCUMENTS

| | | | |
|---|---|---|---|
| 10,617,867 B2 | 4/2020 | Viswanathan et al. | |
| 10,660,702 B2 | 5/2020 | Viswanathan et al. | |
| 10,667,753 B2 | 6/2020 | Werneth et al. | |
| 10,674,929 B2 | 6/2020 | Houben et al. | |
| 10,681,805 B2 | 6/2020 | Weinkam et al. | |
| 10,682,181 B2 | 6/2020 | Cohen et al. | |
| 10,687,892 B2 | 6/2020 | Long et al. | |
| 10,702,178 B2 | 7/2020 | Dahlen et al. | |
| 10,716,477 B2 | 7/2020 | Salvestro et al. | |
| 10,758,304 B2 | 9/2020 | Aujla | |
| 10,765,371 B2 | 9/2020 | Hayam et al. | |
| 10,772,566 B2 | 9/2020 | Aujila | |
| 10,799,281 B2 | 10/2020 | Goertzen et al. | |
| 10,842,558 B2 | 11/2020 | Harlev et al. | |
| 10,842,561 B2 | 11/2020 | Viswanathan et al. | |
| 10,863,914 B2 | 12/2020 | Govari et al. | |
| 10,881,376 B2 | 1/2021 | Shemesh et al. | |
| 10,898,139 B2 | 1/2021 | Guta et al. | |
| 10,905,329 B2 | 2/2021 | Bar-Tal et al. | |
| 10,912,484 B2 | 2/2021 | Ziv-Ari et al. | |
| 10,918,306 B2 | 2/2021 | Govari et al. | |
| 10,939,871 B2 | 3/2021 | Altmann et al. | |
| 10,952,795 B2 | 3/2021 | Cohen et al. | |
| 10,973,426 B2 | 4/2021 | Williams et al. | |
| 10,973,461 B2 | 4/2021 | Baram et al. | |
| 10,987,045 B2 | 4/2021 | Basu et al. | |
| 11,006,902 B1 | 5/2021 | Bonyak et al. | |
| 11,040,208 B1 | 6/2021 | Govari et al. | |
| 11,045,628 B2 | 6/2021 | Beeckler et al. | |
| 11,051,877 B2 | 7/2021 | Sliwa et al. | |
| 11,109,788 B2 | 9/2021 | Rottmann et al. | |
| 11,116,435 B2 | 9/2021 | Urman et al. | |
| 11,129,574 B2 | 9/2021 | Cohen et al. | |
| 11,160,482 B2 | 11/2021 | Solis | |
| 11,164,371 B2 | 11/2021 | Yellin et al. | |
| 2004/0210121 A1 | 10/2004 | Fuimaono et al. | |
| 2006/0009689 A1 | 1/2006 | Fuimaono et al. | |
| 2006/0009690 A1 | 1/2006 | Fuimaono et al. | |
| 2006/0100669 A1 | 5/2006 | Fuimaono et al. | |
| 2007/0093806 A1 | 4/2007 | Desai et al. | |
| 2007/0276212 A1 | 11/2007 | Fuimaono et al. | |
| 2008/0234564 A1 | 9/2008 | Beatty et al. | |
| 2011/0118726 A1 | 5/2011 | De La Rama et al. | |
| 2011/0160574 A1 | 6/2011 | Harlev et al. | |
| 2011/0190625 A1 | 8/2011 | Harlev et al. | |
| 2011/0245756 A1 | 10/2011 | Arora et al. | |
| 2011/0301597 A1 | 12/2011 | McDaniel et al. | |
| 2013/0090651 A1 | 4/2013 | Smith | |
| 2013/0172872 A1 | 7/2013 | Subramaniam et al. | |
| 2013/0172883 A1 | 7/2013 | Lopes et al. | |
| 2013/0178850 A1 | 7/2013 | Lopes et al. | |
| 2013/0190587 A1 | 7/2013 | Lopes et al. | |
| 2013/0296852 A1 | 11/2013 | Madjarov et al. | |
| 2014/0025069 A1 | 1/2014 | Willard et al. | |
| 2014/0052118 A1 | 2/2014 | Laske et al. | |
| 2014/0180147 A1 | 6/2014 | Thakur et al. | |
| 2014/0180151 A1 | 6/2014 | Maskara et al. | |
| 2014/0180152 A1 | 6/2014 | Maskara et al. | |
| 2014/0257069 A1 | 9/2014 | Eliason et al. | |
| 2014/0276712 A1 | 9/2014 | Mallin et al. | |
| 2014/0276733 A1 | 9/2014 | VanScoy et al. | |
| 2014/0309512 A1 | 10/2014 | Govari et al. | |
| 2014/0316502 A1* | 10/2014 | Seeley | A61N 1/05 |
| | | | 607/116 |
| 2015/0011991 A1 | 1/2015 | Buysman et al. | |
| 2015/0045863 A1 | 2/2015 | Litscher et al. | |
| 2015/0080693 A1 | 3/2015 | Solis | |
| 2015/0105770 A1 | 4/2015 | Amit | |
| 2015/0119878 A1 | 4/2015 | Heisel et al. | |
| 2015/0133919 A1 | 5/2015 | McDaniel et al. | |
| 2015/0208942 A1 | 7/2015 | Bar-Tal et al. | |
| 2015/0250424 A1 | 9/2015 | Govari et al. | |
| 2015/0270634 A1 | 9/2015 | Buesseler et al. | |
| 2015/0328448 A1* | 11/2015 | Richter | A61N 1/056 |
| | | | 607/116 |
| 2015/0342532 A1 | 12/2015 | Basu et al. | |
| 2016/0081746 A1 | 3/2016 | Solis | |
| 2016/0113582 A1 | 4/2016 | Altmann et al. | |
| 2016/0113709 A1 | 4/2016 | Maor | |
| 2016/0183877 A1 | 6/2016 | Williams et al. | |
| 2016/0228023 A1 | 8/2016 | Govari | |
| 2016/0228062 A1 | 8/2016 | Altmann et al. | |
| 2016/0278853 A1 | 9/2016 | Ogle et al. | |
| 2016/0302858 A1 | 10/2016 | Bencini | |
| 2016/0338770 A1 | 11/2016 | Bar-Tal et al. | |
| 2017/0027638 A1 | 2/2017 | Solis | |
| 2017/0065227 A1 | 3/2017 | Marrs et al. | |
| 2017/0071543 A1 | 3/2017 | Basu et al. | |
| 2017/0071544 A1 | 3/2017 | Basu et al. | |
| 2017/0071665 A1 | 3/2017 | Solis | |
| 2017/0095173 A1 | 4/2017 | Bar-Tal et al. | |
| 2017/0100187 A1 | 4/2017 | Basu et al. | |
| 2017/0143227 A1 | 5/2017 | Marecki et al. | |
| 2017/0156790 A1 | 6/2017 | Aujla | |
| 2017/0172442 A1 | 6/2017 | Govari | |
| 2017/0172651 A1* | 6/2017 | Gross | A61B 5/021 |
| 2017/0185702 A1 | 6/2017 | Auerbach et al. | |
| 2017/0202515 A1 | 7/2017 | Zrihem et al. | |
| 2017/0221262 A1 | 8/2017 | Laughner et al. | |
| 2017/0224958 A1 | 8/2017 | Cummings et al. | |
| 2017/0265812 A1 | 9/2017 | Williams et al. | |
| 2017/0281031 A1 | 10/2017 | Houben et al. | |
| 2017/0281268 A1 | 10/2017 | Tran et al. | |
| 2017/0296125 A1 | 10/2017 | Altmann et al. | |
| 2017/0296251 A1 | 10/2017 | Wu et al. | |
| 2017/0347959 A1 | 12/2017 | Guta et al. | |
| 2017/0354338 A1 | 12/2017 | Levin et al. | |
| 2017/0354339 A1 | 12/2017 | Zeidan et al. | |
| 2017/0354364 A1 | 12/2017 | Bar-Tal et al. | |
| 2018/0008203 A1 | 1/2018 | Iyun et al. | |
| 2018/0028084 A1 | 2/2018 | Williams et al. | |
| 2018/0049803 A1 | 2/2018 | Solis | |
| 2018/0085064 A1 | 3/2018 | Auerbach et al. | |
| 2018/0132749 A1 | 5/2018 | Govari et al. | |
| 2018/0137687 A1 | 5/2018 | Katz et al. | |
| 2018/0160936 A1 | 6/2018 | Govari et al. | |
| 2018/0160978 A1 | 6/2018 | Cohen et al. | |
| 2018/0168511 A1 | 6/2018 | Hall et al. | |
| 2018/0184982 A1 | 7/2018 | Basu et al. | |
| 2018/0192958 A1 | 7/2018 | Wu | |
| 2018/0206792 A1 | 7/2018 | Auerbach et al. | |
| 2018/0235692 A1 | 8/2018 | Efimov et al. | |
| 2018/0249959 A1 | 9/2018 | Osypka | |
| 2018/0256109 A1 | 9/2018 | Wu et al. | |
| 2018/0279954 A1 | 10/2018 | Hayam et al. | |
| 2018/0303414 A1 | 10/2018 | Toth et al. | |
| 2018/0303546 A1 | 10/2018 | Buysman et al. | |
| 2018/0310987 A1 | 11/2018 | Altmann et al. | |
| 2018/0311497 A1 | 11/2018 | Viswanathan et al. | |
| 2018/0338722 A1 | 11/2018 | Altmann et al. | |
| 2018/0344188 A1 | 12/2018 | Govari | |
| 2018/0344202 A1 | 12/2018 | Bar-Tal et al. | |
| 2018/0344251 A1 | 12/2018 | Harlev et al. | |
| 2018/0344393 A1 | 12/2018 | Gruba et al. | |
| 2018/0360534 A1 | 12/2018 | Teplitsky et al. | |
| 2018/0365355 A1 | 12/2018 | Auerbach et al. | |
| 2019/0000540 A1 | 1/2019 | Cohen et al. | |
| 2019/0008582 A1 | 1/2019 | Govari et al. | |
| 2019/0015007 A1 | 1/2019 | Rottmann et al. | |
| 2019/0030328 A1 | 1/2019 | Stewart et al. | |
| 2019/0053708 A1 | 2/2019 | Gliner | |
| 2019/0059766 A1 | 2/2019 | Houben et al. | |
| 2019/0069950 A1 | 3/2019 | Viswanathan et al. | |
| 2019/0069954 A1 | 3/2019 | Cohen et al. | |
| 2019/0117111 A1 | 4/2019 | Osadchy et al. | |
| 2019/0117303 A1 | 4/2019 | Claude et al. | |
| 2019/0117315 A1 | 4/2019 | Keyes et al. | |
| 2019/0125439 A1 | 5/2019 | Rohl et al. | |
| 2019/0133552 A1 | 5/2019 | Shemesh et al. | |
| 2019/0142293 A1 | 5/2019 | Solis | |
| 2019/0164633 A1 | 5/2019 | Ingel et al. | |
| 2019/0167137 A1 | 6/2019 | Bar-Tal et al. | |
| 2019/0167140 A1 | 6/2019 | Williams et al. | |
| 2019/0188909 A1 | 6/2019 | Yellin et al. | |

(56)  References Cited

U.S. PATENT DOCUMENTS

| | | |
|---|---|---|
| 2019/0201664 A1 | 7/2019 | Govari |
| 2019/0209089 A1 | 7/2019 | Baram et al. |
| 2019/0216346 A1 | 7/2019 | Ghodrati et al. |
| 2019/0216347 A1 | 7/2019 | Ghodrati et al. |
| 2019/0231421 A1 | 8/2019 | Viswanathan et al. |
| 2019/0231423 A1 | 8/2019 | Weinkam et al. |
| 2019/0239811 A1 | 8/2019 | Just et al. |
| 2019/0246935 A1 | 8/2019 | Govari et al. |
| 2019/0298442 A1 | 10/2019 | Ogata et al. |
| 2019/0314083 A1 | 10/2019 | Herrera et al. |
| 2019/0328260 A1 | 10/2019 | Zeidan et al. |
| 2019/0343580 A1 | 11/2019 | Nguyen et al. |
| 2020/0000518 A1 | 1/2020 | Kiernan et al. |
| 2020/0008705 A1 | 1/2020 | Ziv-Ari et al. |
| 2020/0008869 A1 | 1/2020 | Byrd |
| 2020/0009378 A1 | 1/2020 | Stewart et al. |
| 2020/0015890 A1 | 1/2020 | To et al. |
| 2020/0022653 A1 | 1/2020 | Moisa |
| 2020/0029845 A1 | 1/2020 | Baram et al. |
| 2020/0046421 A1 | 2/2020 | Govari |
| 2020/0046423 A1 | 2/2020 | Viswanathan et al. |
| 2020/0060569 A1 | 2/2020 | Tegg |
| 2020/0077959 A1 | 3/2020 | Altmann et al. |
| 2020/0093539 A1 | 3/2020 | Long et al. |
| 2020/0129089 A1 | 4/2020 | Gliner et al. |
| 2020/0129125 A1 | 4/2020 | Govari et al. |
| 2020/0129128 A1 | 4/2020 | Gliner et al. |
| 2020/0179650 A1 | 6/2020 | Beeckler et al. |
| 2020/0196896 A1 | 6/2020 | Solis |
| 2020/0205689 A1 | 7/2020 | Squires et al. |
| 2020/0205690 A1 | 7/2020 | Williams et al. |
| 2020/0205737 A1 | 7/2020 | Beeckler |
| 2020/0205876 A1 | 7/2020 | Govari |
| 2020/0205892 A1 | 7/2020 | Viswanathan et al. |
| 2020/0206461 A1 | 7/2020 | Govari et al. |
| 2020/0206498 A1 | 7/2020 | Arora et al. |
| 2020/0289197 A1 | 9/2020 | Viswanathan et al. |
| 2020/0297234 A1 | 9/2020 | Houben et al. |
| 2020/0297281 A1 | 9/2020 | Basu et al. |
| 2020/0305726 A1 | 10/2020 | Salvestro et al. |
| 2020/0305946 A1 | 10/2020 | Desimone et al. |
| 2020/0397328 A1 | 12/2020 | Altmann et al. |
| 2020/0398048 A1 | 12/2020 | Krimsky et al. |
| 2021/0015549 A1 | 1/2021 | Haghighi-Mood et al. |
| 2021/0022684 A1 | 1/2021 | Govari et al. |
| 2021/0045805 A1 | 2/2021 | Govari et al. |
| 2021/0059549 A1 | 3/2021 | Urman et al. |
| 2021/0059550 A1 | 3/2021 | Urman et al. |
| 2021/0059608 A1 | 3/2021 | Beeckler et al. |
| 2021/0059743 A1 | 3/2021 | Govari |
| 2021/0059747 A1 | 3/2021 | Krans et al. |
| 2021/0077184 A1 | 3/2021 | Basu et al. |
| 2021/0082157 A1 | 3/2021 | Rosenberg et al. |
| 2021/0085200 A1 | 3/2021 | Auerbach et al. |
| 2021/0085204 A1 | 3/2021 | Auerbach et al. |
| 2021/0085215 A1 | 3/2021 | Auerbach et al. |
| 2021/0085387 A1 | 3/2021 | Amit et al. |
| 2021/0093292 A1 | 4/2021 | Baram et al. |
| 2021/0093294 A1 | 4/2021 | Shemesh et al. |
| 2021/0093374 A1 | 4/2021 | Govari et al. |
| 2021/0093377 A1 | 4/2021 | Herrera et al. |
| 2021/0100612 A1 | 4/2021 | Baron et al. |
| 2021/0113822 A1 | 4/2021 | Beeckler et al. |
| 2021/0127999 A1 | 5/2021 | Govari et al. |
| 2021/0128010 A1 | 5/2021 | Govari et al. |
| 2021/0133516 A1 | 5/2021 | Govari et al. |
| 2021/0145282 A1 | 5/2021 | Bar-Tal et al. |
| 2021/0161592 A1 | 6/2021 | Altmann et al. |
| 2021/0162210 A1 | 6/2021 | Altmann et al. |
| 2021/0169421 A1 | 6/2021 | Govari |
| 2021/0169550 A1 | 6/2021 | Govari et al. |
| 2021/0169567 A1 | 6/2021 | Govari et al. |
| 2021/0169568 A1 | 6/2021 | Govari et al. |
| 2021/0177294 A1 | 6/2021 | Gliner et al. |
| 2021/0177356 A1 | 6/2021 | Gliner et al. |
| 2021/0177503 A1 | 6/2021 | Altmann et al. |
| 2021/0178166 A1 | 6/2021 | Govari et al. |
| 2021/0186363 A1 | 6/2021 | Gliner et al. |
| 2021/0186604 A1 | 6/2021 | Altmann et al. |
| 2021/0187241 A1 | 6/2021 | Govari et al. |
| 2021/0196353 A1* | 7/2021 | Gee ............... A61B 17/320092 |
| 2021/0196372 A1 | 7/2021 | Altmann et al. |
| 2021/0196394 A1 | 7/2021 | Govari et al. |
| 2021/0212591 A1 | 7/2021 | Govari et al. |
| 2021/0219904 A1 | 7/2021 | Yarnitsky et al. |
| 2021/0278936 A1 | 9/2021 | Katz et al. |
| 2021/0282659 A1 | 9/2021 | Govari et al. |
| 2021/0307815 A1 | 10/2021 | Govari et al. |
| 2021/0308424 A1 | 10/2021 | Beeckler et al. |
| 2021/0338319 A1 | 11/2021 | Govari et al. |

FOREIGN PATENT DOCUMENTS

| | | |
|---|---|---|
| EP | 0668740 A1 | 8/1995 |
| EP | 0644738 B1 | 3/2000 |
| EP | 0727183 B1 | 11/2002 |
| EP | 0727184 B1 | 12/2002 |
| EP | 2783651 A1 | 10/2014 |
| EP | 2699151 B1 | 11/2015 |
| EP | 2699152 B1 | 11/2015 |
| EP | 2699153 B1 | 12/2015 |
| EP | 2498706 B1 | 4/2016 |
| EP | 2578173 B1 | 6/2017 |
| EP | 3181082 A1 | 6/2017 |
| EP | 3238645 A1 | 11/2017 |
| EP | 2884931 B1 | 1/2018 |
| EP | 2349440 B1 | 8/2019 |
| EP | 3318211 B1 | 12/2019 |
| EP | 3581135 A1 | 12/2019 |
| EP | 2736434 B1 | 2/2020 |
| EP | 3451962 B1 | 3/2020 |
| EP | 3972510 A1 | 3/2022 |
| WO | 9421167 A1 | 9/1994 |
| WO | 9421169 A1 | 9/1994 |
| WO | 9625095 A1 | 8/1996 |
| WO | 9634560 A1 | 11/1996 |
| WO | 0182814 B1 | 5/2002 |
| WO | 2004087249 A2 | 10/2004 |
| WO | 2012100185 A2 | 7/2012 |
| WO | 2013052852 A1 | 4/2013 |
| WO | 2013162884 A1 | 10/2013 |
| WO | 2013173917 A1 | 11/2013 |
| WO | 2013176881 A1 | 11/2013 |
| WO | 2014158708 A1 | 10/2014 |
| WO | 2014176205 A1 | 10/2014 |
| WO | 2016019760 A1 | 2/2016 |
| WO | 2016044687 A1 | 3/2016 |
| WO | 2018111600 A1 | 6/2018 |
| WO | 2018191149 A1 | 10/2018 |
| WO | 2019084442 A1 | 5/2019 |
| WO | 2019143960 A1 | 7/2019 |
| WO | 2020026217 A1 | 2/2020 |
| WO | 2020206328 A1 | 10/2020 |

* cited by examiner

Start

802 — Aligning a spine with an electrode

804 — Inserting the spine into a lumen of the electrode

806 — Aligning a locking stub of the electrode with the aperture of the spine

808 — Crimping the electrode onto the spine such that the locking stub extends at least partially into the aperture End

BARREL ELECTRODES FOR A BASKET CATHETER, AND METHODS OF THE SAME

CLAIM OF PRIORITY

This application claims the benefit of priority under 35 U.S.C. § 119 to U.S. Provisional Patent Application No. 63/336,072 filed on Apr. 28, 2022, which is hereby incorporated by reference as if set forth in full herein.

FIELD

The present invention relates generally to medical devices, and in particular catheters with electrodes, and further relates to, but not exclusively, catheters suitable for use to induce irreversible electroporation (IRE) of cardiac tissues.

BACKGROUND

Cardiac arrhythmias, such as atrial fibrillation (AF), occur when regions of cardiac tissue abnormally conduct electric signals to adjacent tissue. This disrupts the normal cardiac cycle and causes asynchronous rhythm. Certain procedures exist for treating arrhythmia, including surgically disrupting the origin of the signals causing the arrhythmia and disrupting the conducting pathway for such signals. By selectively ablating cardiac tissue by application of energy via a catheter, it is sometimes possible to cease or modify the propagation of unwanted electrical signals from one portion of the heart to another.

Many current ablation approaches in the art utilize radiofrequency (RF) electrical energy to heat tissue. RF ablation can have certain risks related to thermal heating which can lead to tissue charring, burning, steam pop, phrenic nerve palsy, pulmonary vein stenosis, and esophageal fistula.

Cryoablation is an alternative approach to RF ablation that generally reduces thermal risks associated with RF ablation. Maneuvering cryoablation devices and selectively applying cryoablation, however, is generally more challenging compared to RF ablation; therefore cryoablation is not viable in certain anatomical geometries which may be reached by electrical ablation devices.

Some ablation approaches use irreversible electroporation (IRE) to ablate cardiac tissue using nonthermal ablation methods. IRE delivers short pulses of high voltage to tissues and generates an unrecoverable permeabilization of cell membranes. Delivery of IRE energy to tissues using multi-electrode catheters was previously proposed in the patent literature. Examples of systems and devices configured for IRE ablation are disclosed in U.S. Patent Pub. No. 2021/0161592A1, 2021/0169550A1, 2021/0169567A1, 2021/0169568A1, 2021/0177503A1, 2021/0186604A1 and 2021/0196372A1, each of which is incorporated by reference in its entirety into this application as if set forth in full and is attached in the appendix to priority application U.S. 63/336,072.

Regions of cardiac tissue can be mapped by a catheter to identify the abnormal electrical signals. The same or different catheter can be used to perform ablation. Some example catheters include a number of spines with electrodes positioned thereon. The electrodes are generally attached to the spines and secured in place by soldering, welding, or using an adhesive. Due to the small size of the spines and the electrodes, however, soldering, welding, or adhering the electrodes to the spines can be a difficult task, increasing the manufacturing time and cost and the chances that the electrode fails due to an improper bond or misalignment. What is needed, therefore, are systems and methods of attaching an electrode to a spine of a basket assembly without the need for soldering, welding, or using adhesive.

SUMMARY

There is provided, in accordance with an example of the present invention, an electrode for a medical probe having an elongated body. At least a portion of the elongated body can be electrically conductive. The elongated body can define a lumen that extends through the elongated body along a longitudinal axis of the elongated body. The electrode can include a locking stub that extends at least partially into the lumen so that the locking stub is locked to a member inserted into the lumen. In this way, the presently disclosed technology can be used to secure the electrodes to the spines without requiring solder, weld, or adhesives.

The electrode can be crimped towards the longitudinal axis. The electrode can include a substantially rounded outer surface prior to being crimped and a substantially flat outer surface after being crimped.

The locking stub can have a substantially rounded cross section, a substantially rectangular cross section, and/or at least a portion of the locking stub can include a substantially triangular cross section.

The locking stub can extend a length of the elongated body.

The elongated body can further include an insulative material that can be configured to electrically isolate the electrode from the member inserted into the lumen.

The lumen can be a first lumen and the elongated body can further define a second lumen configured to receive a wire. The wire can be electrically coupled to the electrode.

There is provided, in accordance with another example of the present invention, a medical probe. The medical probe can include a tubular shaft having a proximal end and a distal end. The tubular shaft can extend along a longitudinal axis. The medical probe can include an expandable basket assembly coupled to the distal end of the tubular shaft.

The expandable basket assembly can include a plurality of electrodes. Each electrode of the plurality of electrodes can define a lumen extending therethrough and a locking stub extending at least partially into the lumen.

The expandable basket assembly can include a plurality of spines extending along the longitudinal axis and configured to bow radially outward from the longitudinal axis when the expandable basket assembly is transitioned from a collapsed form to an expanded form. Each spine of the plurality of spines can pass through a lumen of an electrode of the plurality of electrodes. Each spine of the plurality of spines can define an aperture that extends therethrough from a first side of the spine to a second side of the spine. The aperture can be configured to receive the locking stub of the electrode such that when the electrode is mechanically coupled to the spine, the locking stub extends through the aperture preventing the electrode from sliding distally or proximally along the spine.

Each electrode of the plurality of electrodes can be crimped to the spine. Each electrode of the plurality of electrodes can have a substantially rounded outer surface prior to being crimped to the spine and a substantially flat outer surface after being crimped to the spine.

The locking stub can have a substantially rounded cross section, a substantially rectangular cross section, and/or at least a portion of the locking stub can include a substantially triangular cross section.

Each electrode can include an insulative material that can be configured to electrically isolate the electrode from the spine. Alternatively, or in addition, each spine can include an insulative material and/or an insulative material can be disposed between the electrode and the spine to electrically isolate the electrode from the spine.

The lumen of each electrode can be a first lumen and each electrode can further define a second lumen that is configured to receive a wire of the medical probe. The wire can be electrically coupled to the electrode. The wire can be insulated from the spine.

Each spine can include a first electrode and a second electrode both mechanically coupled to the spine. The spine can define a first aperture configured to receive a locking stub of the first electrode and a second aperture configured to receive a locking stub of the second electrode. The first and second apertures can be configured to prevent the first and second electrodes from sliding proximally or distally along a length of the spine when the first and second electrodes are mechanically coupled to the spine, respectively. An interface between the locking stub of the electrode and the spine at the aperture can include an interference fitting.

The spine can include a material selected from a group consisting of nitinol, cobalt chromium, stainless steel, titanium and combinations thereof. Alternatively, or in addition, the spine can include a polymer material.

The plurality of electrodes can be configured to deliver electrical pulses for irreversible electroporation. The pulses can have a peak voltage of at least 900 volts (V). The plurality of electrodes can be configured for mapping electrophysiological characteristics of cardiac tissue.

The medical probe can include spray ports that can be configured to deliver an irrigation fluid to the plurality of electrodes.

The disclosed technology can include a method of constructing a medical probe. The method can include aligning a spine of an expandable basket assembly with an electrode of the expandable basket assembly. The spine can include a proximal end, a distal end, and define an aperture extending therethrough. The method can include inserting the spine into a lumen of the electrode and aligning a locking stub of the electrode with the aperture. The method can include crimping the electrode onto the spine such that the locking stub extends at least partially into the aperture to prevent the electrode from sliding proximally or distally along the spine.

The electrode can have a substantially rounded outer surface prior to being crimped to the spine and a substantially flat outer surface after being crimped to the spine.

The locking stub can have a substantially rounded cross section, a substantially rectangular cross section, and/or at least a portion of the locking stub can include a substantially triangular cross section.

The electrode can include an insulative material configured to electrically isolate the electrode from the spine. Alternatively, or in addition, the spine can include an insulative material or an insulative material can be disposed between the electrode and the spine to electrically isolate the electrode from the spine.

The lumen can be a first lumen and the method can further include aligning a wire of the medical probe with a second lumen of the electrode, inserting the wire into the second lumen, and coupling the wire to the electrode such that the wire is in electrical communication with the electrode. The wire can be insulated from the spine.

An interface between the locking stub of the electrode and the spine at the aperture can be an interference fitting. The spine can be a material selected from a group consisting of nitinol, cobalt chromium, stainless steel, titanium. Alternatively, or in addition, the spine can include a polymer material.

The aperture of the spine can be a first aperture. The spine can further define a second aperture. The method can further include aligning the spine with a second electrode of the expandable basket assembly, inserting the spine into a lumen of the second electrode, aligning a locking stub of the second electrode with the second aperture, and crimping the second electrode onto the spine such that the locking stub extends at least partially into the second aperture to prevent the second electrode from sliding proximally or distally along the spine.

BRIEF DESCRIPTION OF THE DRAWINGS

FIGS. 3A and 3B are schematic pictorial illustrations showing exploded views of a tubular shaft and spines of the basket assembly to illustrate how the spines can be assembled together with the tubular shaft, in accordance with an embodiment of the present invention;

FIG. 4A is a schematic pictorial illustration showing a front perspective view of an electrode before being crimped while

FIG. 5A is a schematic pictorial illustration showing a side perspective view of an electrode before being crimped while

FIG. 6A is a schematic pictorial illustration showing a front perspective view of an electrode and a spine before the electrode is crimped to the spine while

DETAILED DESCRIPTION

Figure 1:
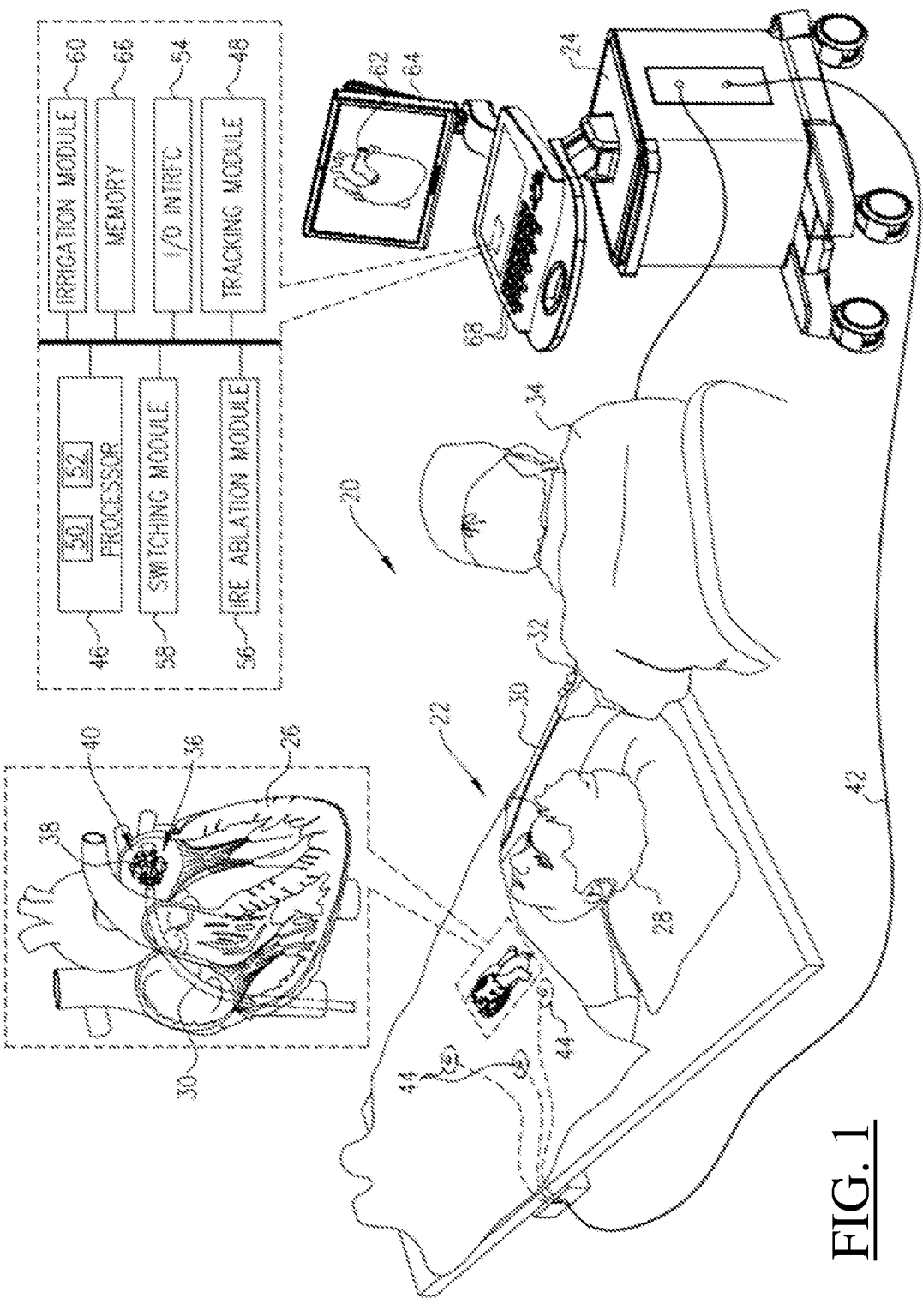
FIG. 1 is a schematic pictorial illustration of a medical system including a medical probe whose distal end includes a basket assembly with electrodes, in accordance with an embodiment of the present invention.

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±10% of the recited value, e.g. "about 90%" may refer to the range of values from 81% to 99%. In addition, as used herein, the terms "patient," "host," "user," and "subject" refer to any human or animal subject and are not intended to limit the systems or methods to human use, although use of the subject invention in a human patient represents a preferred embodiment. As well, the term "proximal" indicates a location closer to the operator or physician whereas "distal" indicates a location further away to the operator or physician.

As discussed herein, vasculature of a "patient," "host," "user," and "subject" can be vasculature of a human or any animal. It should be appreciated that an animal can be a variety of any applicable type, including, but not limited thereto, mammal, veterinarian animal, livestock animal or pet type animal, etc. As an example, the animal can be a laboratory animal specifically selected to have certain characteristics similar to a human (e.g., rat, dog, pig, monkey, or the like). It should be appreciated that the subject can be any applicable human patient, for example.

As discussed herein, "operator" can include a doctor, surgeon, technician, scientist, or any other individual or delivery instrumentation associated with delivery of a multi-electrode catheter for the treatment of drug refractory atrial fibrillation to a subject.

As discussed herein, the term "ablate" or "ablation", as it relates to the devices and corresponding systems of this disclosure, refers to components and structural features configured to reduce or prevent the generation of erratic cardiac signals in the cells by utilizing non-thermal energy, such as irreversible electroporation (IRE), sometimes referred to interchangeably as pulsed electric field (PEF) and pulsed field ablation (PFA). Ablating or ablation as it relates to the devices and corresponding systems of this disclosure is used throughout this disclosure in reference to non-thermal ablation of cardiac tissue for certain conditions including, but not limited to, arrhythmias, atrial flutter ablation, pulmonary vein isolation, supraventricular tachy-cardia ablation, and ventricular tachycardia ablation. The term "ablate" or "ablation" also includes known methods, devices, and systems to achieve various forms of bodily tissue ablation as understood by a person skilled in the relevant art.

As discussed herein, the terms "bipolar" and "unipolar" when used to refer to ablation schemes describe ablation schemes which differ with respect to electrical current path and electric field distribution. "Bipolar" refers to ablation scheme utilizing a current path between two electrodes that are both positioned at a treatment site; current density and electric flux density is typically approximately equal at each of the two electrodes. "Unipolar" refers to ablation scheme utilizing a current path between two electrodes where one electrode having a high current density and high electric flux density is positioned at a treatment site, and a second electrode having comparatively lower current density and lower electric flux density is positioned remotely from the treatment site.

As discussed herein, the terms "tubular" and "tube" are to be construed broadly and are not limited to a structure that is a right cylinder or strictly circumferential in cross-section or of a uniform cross-section throughout its length. For example, the tubular structures are generally illustrated as a substantially right cylindrical structure. However, the tubular structures may have a tapered or curved outer surface without departing from the scope of the present disclosure.

The present disclosure is related to systems, method or uses and devices for IRE ablation of cardiac tissue to treat cardiac arrhythmias. Ablative energies are typically provided to cardiac tissue by a tip portion of a catheter which can deliver ablative energy alongside the tissue to be ablated. Some example catheters include three-dimensional structures at the tip portion and are configured to administer ablative energy from various electrodes positioned on the three-dimensional structures. Ablative procedures incorporating such example catheters can be visualized using fluoroscopy.

Ablation of cardiac tissue using application of a thermal technique, such as radio frequency (RF) energy and cryoablation, to correct a malfunctioning heart is a well-known procedure. Typically, to successfully ablate using a thermal technique, cardiac electropotentials need to be measured at various locations of the myocardium. In addition, temperature measurements during ablation provide data enabling the efficacy of the ablation. Typically, for an ablation procedure using a thermal technique, the electropotentials and the temperatures are measured before, during, and after the actual ablation. RF approaches can have risks that can lead to tissue charring, burning, steam pop, phrenic nerve palsy, pulmonary vein stenosis, and esophageal fistula. Cryoablation is an alternative approach to RF ablation that can reduce some thermal risks associated with RF ablation. However maneuvering cryoablation devices and selectively applying cryoablation is generally more challenging compared to RF ablation; therefore cryoablation is not viable in certain anatomical geometries which may be reached by electrical ablation devices.

While RF ablation and cryoablation, are based on thermal energy transfer to induce local tissue necrosis, the solution of this disclosure can resolve these and other problems by utilizing irreversible electroporation (IRE), sometimes referred to interchangeably as pulsed electric field (PEF) ablation and pulsed field ablation (PFA). IRE as discussed in this disclosure is a non-thermal cell death technology that can be used for ablation of atrial arrhythmias. To ablate using IRE/PEF, biphasic voltage pulses are applied to disrupt cellular structures of myocardium. The biphasic pulses are non-sinusoidal and can be tuned to target cells based on electrophysiology of the cells. In contrast, to ablate using RF, a sinusoidal voltage waveform is applied to produce heat at the treatment area, indiscriminately heating all cells in the treatment area. IRE therefore has the capability to spare adjacent heat sensitive structures or tissues which would be of benefit in the reduction of possible complications known with ablation or isolation modalities. Additionally, or alternatively, monophasic pulses can be utilized.

Electroporation can be induced by applying a pulsed electric field across biological cells to cause reversable (temporary) or irreversible (permanent) creation of pores in the cell membrane. The cells have a transmembrane electrostatic potential that is increased above a resting potential upon application of the pulsed electric field. While the transmembrane electrostatic potential remains below a threshold potential, the electroporation is reversable, meaning the pores can close when the applied pulse electric field is removed, and the cells can self-repair and survive. If the transmembrane electrostatic potential increases beyond the threshold potential, the electroporation is irreversible, and the cells become permanently permeable. As a result, the cells die due to a loss of homeostasis and typically die by apoptosis. Generally, cells of differing types have differing threshold potential. For instance, heart cells have a threshold potential of approximately 500 V/cm, whereas for bone it is 3000 V/cm. These differences in threshold potential allow IRE to selectively target tissue based on threshold potential.

The solution of this disclosure includes systems and methods for applying electrical signals from catheter electrodes positioned in the vicinity of myocardial tissue to generate a pulsed electric field effective to induce electroporation in the myocardial tissue. The systems and methods can be effective to ablate targeted tissue by inducing irreversible electroporation. In some examples, the systems and methods can be effective to induce reversible electroporation as part of a diagnostic procedure. Reversible electroporation occurs when the electricity applied with the electrodes is below the electric field threshold of the target tissue allowing cells to repair. Reversible electroporation does not kill the cells but allows a physician to see the effect of reversible electroporation on electrical activation signals in the vicinity of the target location. Example systems and methods for reversible electroporation is disclosed in U.S. Patent Publication 2021/0162210, the entirety of which is incorporated by reference in its entirety into this application as if set forth in full and is attached in the appendix to priority application U.S. 63/336,072.

The pulsed electric field, and its effectiveness to induce reversible and/or irreversible electroporation, can be affected by physical parameters of the system and biphasic pulse parameters of the electrical signal. Physical parameters can include electrode contact area, electrode spacing, electrode geometry, etc. examples presented herein generally include physical parameters adapted to effectively induce reversible and/or irreversible electroporation. Biphasic pulse parameters of the electrical signal can include voltage amplitude, pulse duration, pulse interphase delay, inter-pulse delay, total application time, delivered energy, etc. In some examples, parameters of the electrical signal can be adjusted to induce both reversible and irreversible electroporation given the same physical parameters. Examples of various systems and methods of ablation including IRE are presented in U.S. Patent Publications 2021/0161592A1, 2021/0169550A1, 2021/0169567A1, 2021/0169568A1, 2021/0177503A1, 2021/0186604A1 and 2021/0196372A1, each of which is incorporated by reference in its entirety into this application as if set forth in full and is attached in the appendix to priority application U.S. 63/336,072.

To deliver pulsed field ablation (PFA) in an IRE (irreversible electroporation) procedure, electrodes should contact the tissue being ablated with a sufficiently large surface area. As described hereinbelow, the medical probe includes a flexible insertion tube having proximal and distal ends, and a basket assembly at the distal end of the flexible insertion tube.

The basket assembly includes at least one spine and a plurality of electrodes, each given electrode having a lumen therethrough fitting a given spine. The electrodes are crimped to the spine and locked in place with a locking stub to prevent the electrodes from sliding proximally or distally along the length of the spine.

FIG. 1 is a schematic, pictorial illustration of a medical system 20 including a medical probe 22 and a control console 24, in accordance with an embodiment of the present invention. Medical system 20 may be based, for example, on the CARTO® system, produced by Biosense Webster Inc. of 31 Technology Drive, Suite 200, Irvine, CA 92618 USA. In embodiments described hereinbelow, medical probe 22 can be used for diagnostic or therapeutic treatment, such as for performing ablation procedures in a heart 26 of a patient 28. Alternatively, medical probe 22 may be used, mutatis mutandis, for other therapeutic and/or diagnostic purposes in the heart or in other body organs.

Medical probe 22 includes a flexible insertion tube 30 and a handle 32 coupled to a proximal end of the insertion tube. During a medical procedure, a medical professional 34 can insert probe 22 through the vascular system of patient 28 so that a distal end 36 of the medical probe enters a body cavity such as a chamber of heart 26. Upon distal end 36 entering the chamber of heart 26, medical professional 34 can deploy a basket assembly 38 affixed to distal end 36. Basket assembly 38 can include a plurality of electrodes 40 affixed to a plurality of spines, as described in the description referencing FIGS. 2A and 2B hereinbelow. To start performing a medical procedure such as irreversible electroporation (IRE) ablation, medical professional 34 can manipulate handle 32 to position distal end 36 so that electrodes 40 engage cardiac tissue at a desired location or locations. Upon positioning the distal end 36 so that electrodes 40 can engage cardiac tissue, the medical professional 34 can activate the medical probe 22 such that electrical pulses are delivered by the electrodes 40 to perform the IRE ablation.

In the configuration shown in FIG. 1, control console 24 is connected, by a cable 42, to body surface electrodes, which typically include adhesive skin patches 44 that are affixed to patient 28. Control console 24 includes a processor 46 that, in conjunction with a tracking module 48, determines location coordinates of distal end 36 inside heart 26. Location coordinates can be determined based on electromagnetic position sensor output signals provided from the distal portion of the catheter when in the presence of a generated magnetic field. Location coordinates can additionally, or alternatively be based on impedances and/or currents measured between adhesive skin patches 44 and electrodes 40 that are affixed to basket assembly 38. In addition to being used as location sensors during a medical procedure, electrodes 40 may perform other tasks such as ablating tissue in the heart.

As described hereinabove, in conjunction with tracking module 48, processor 46 may determine location coordinates of distal end 36 inside heart 26 based on impedances and/or currents measured between adhesive skin patches 44 and electrodes 40. Such a determination is typically after a calibration process relating the impedances or currents to known locations of the distal end has been performed. While embodiments presented herein describe electrodes 40 that are (also) configured to deliver IRE ablation energy to tissue in heart 26, configuring electrodes 40 to deliver any other type of ablation energy to tissue in any body cavity is considered to be within the spirit and scope of the present invention. Furthermore, although described in the context of being electrodes 40 that are configured to deliver IRE ablation energy to tissue in the heart 26, one skilled in the art will appreciate that the disclosed technology can be applicable to electrodes used for mapping and/or determining various characteristics of an organ or other part of the patient's 28 body.

Processor 46 may include real-time noise reduction circuitry 50 typically configured as a field programmable gate array (FPGA), followed by an analog-to-digital (A/D) signal conversion integrated circuit 52. The processor can be programmed to perform one or more algorithms and uses circuitry 50 and circuit 52 as well as features of modules to enable the medical professional 34 to perform the IRE ablation procedure.

Control console 24 also includes an input/output (I/O) communications interface 54 that enables control console 24 to transfer signals from, and/or transfer signals to electrodes 40 and adhesive skin patches 44. In the configuration shown in FIG. 1, control console 24 additionally includes an IRE ablation module 56 and a switching module 58.

IRE ablation module 56 is configured to generate IRE pulses having peak power in the range of tens of kilowatts. In some examples, the electrodes 40 are configured to deliver electrical pulses having a peak voltage of at least 900 volts (V). The medical system 20 performs IRE ablation by delivering IRE pulses to electrodes 40. Preferably, the medical system 20 delivers biphasic pulses between electrodes 40 on the spine. Additionally, or alternatively, the medical system 20 delivers monophasic pulses between at least one of the electrodes 40 and a skin patch.

In order to dissipate the heat and to improve the efficiency of the ablation process, system 20 supplies irrigation fluid (e.g., a saline solution) to distal end 36 via a channel (not shown) in insertion tube 30. Control console 24 includes an irrigation module 60 to monitor and control irrigation parameters, such as the pressure and the temperature of the irrigation fluid.

Based on signals received from electrodes 40 and/or adhesive skin patches 44, processor 46 can generate an electroanatomical map 62 that shows the location of distal end 36 in the patient's body. During the procedure, processor 46 can present map 62 to medical professional 34 on a display 64, and store data representing the electroanatomical map in a memory 66. Memory 66 may include any suitable volatile and/or non-volatile memory, such as random-access memory or a hard disk drive.

In some embodiments, medical professional 34 can manipulate map 62 using one or more input devices 68. In alternative embodiments, display 64 may include a touch-screen that can be configured to accept inputs from medical professional 34, in addition to presenting map 62.

Figure 2A:
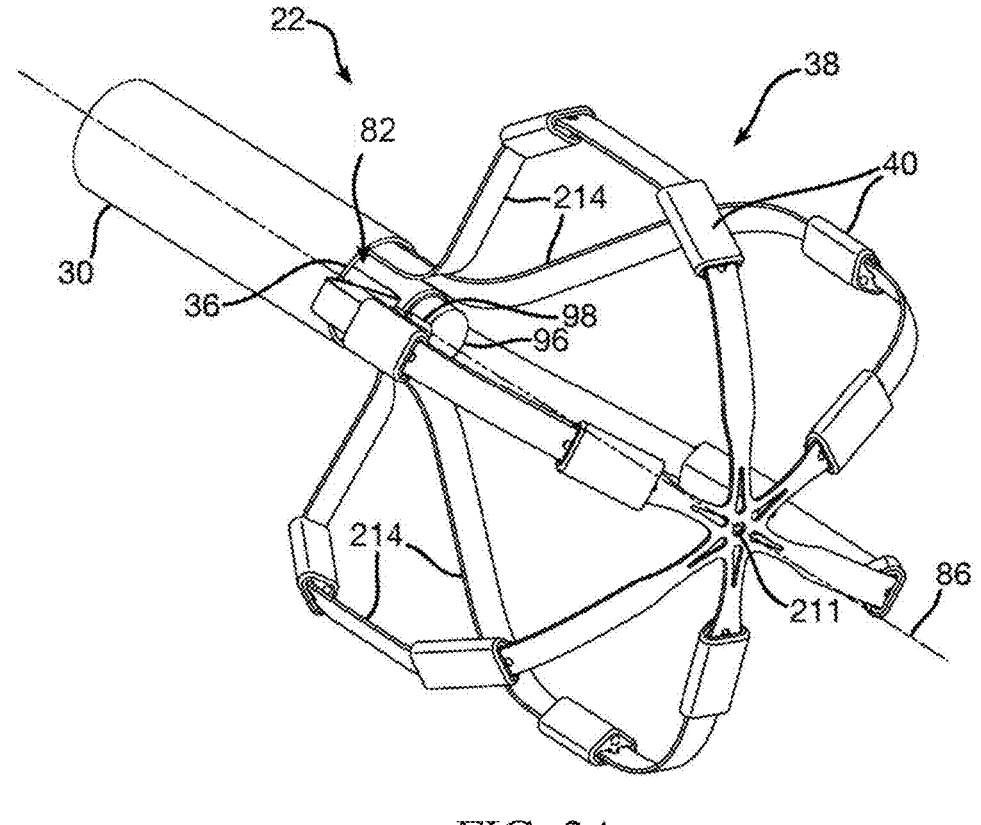
FIG. 2A is a schematic pictorial illustration showing a perspective view of a medical probe in an expanded form, in accordance with an embodiment of the present invention.
Figure 2B:
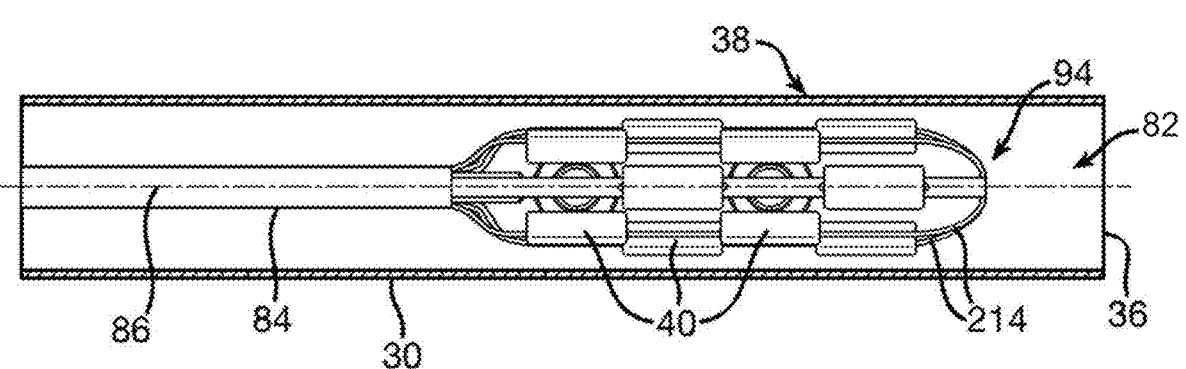
FIG. 2B is a schematic pictorial illustration showing a side view of a medical probe in a collapsed form, in accordance with the disclosed technology.

FIG. 2A is a schematic pictorial illustration showing a perspective view of a medical probe 22 having a basket assembly 38 in an expanded form when unconstrained, such as by being advanced out of an insertion tube lumen at a distal end 36 of an insertion tube 30'. FIG. 2B shows the basket assembly in a collapsed form within insertion tube 30. In the expanded form (FIG. 2A), the spines 214 bow radially outwardly from a longitudinal axis 86 of the medical probe 22 and in the collapsed form (FIG. 2B) the spines are arranged generally along the longitudinal axis 86 of the medical probe 22.

As shown in FIG. 2A, basket assembly 38 includes a plurality of flexible spines 214 that are formed at the end of a tubular shaft 84 and are connected at both ends. During a medical procedure, medical professional 34 can deploy basket assembly 38 by extending tubular shaft 84 from insertion tube 30 causing the basket assembly 38 to exit the insertion tube and transition to the expanded form. Spines 214 may have elliptical (e.g., circular) or rectangular (that may appear to be flat) cross-sections, and include a flexible, resilient material (e.g., a shape-memory alloy such as nickel-titanium (also known as Nitinol), cobalt chromium, stainless steel, titanium, or any other suitable material or combinations of materials).

In embodiments described herein, electrodes 40 can be configured to deliver ablation energy (RF and/or IRE) to tissue in heart 26. For example, the electrodes 40 can be configured to deliver 20-30 amps of electrical current to cardiac tissue to facilitate ablation of the cardiac tissue. Furthermore, the electrodes 40 can be configured for bipolar or unipolar ablation schemes depending on the particular application. Alternatively, or in addition, the electrodes can be used to determine the location of basket assembly 38 and/or to measure a physiological property such as local surface electrical potentials at respective locations on tissue in heart 26.

Examples of materials ideally suited for forming electrodes 40 include gold, platinum, and palladium (and their respective alloys). These materials also have high thermal conductivity which allows the minimal heat generated on the tissue (i.e., by the ablation energy delivered to the tissue) to be conducted through the electrodes to the back side of the electrodes (i.e., the portions of the electrodes on the inner sides of the spines), and then to the blood pool in heart 26.

Basket assembly 38 has a distal end 94 and includes a stem 96 that extends longitudinally from a distal end 36 of shaft 84 towards distal end 94 of basket assembly 38. As described supra, control console 24 includes irrigation module 60 that delivers irrigation fluid to distal end 36. Stem 96 includes multiple spray ports 98, wherein each given spray port 98 can be angled to aim delivery of the irrigation fluid to either a given electrode 40 or to tissue in heart 26.

Since electrodes 40 do not include spray ports that deliver irrigation fluid, the configuration described hereinabove enables heat to be transferred from the tissue (i.e., during an ablation procedure) to the portion of the electrodes 40 on the inner side of the spines 214, and the electrodes 40 can be cooled by aiming the irrigation fluid, via spray ports 98, at the portion of the electrodes 40 on the inner side of the spines 214.

Figures 3A, 3B:
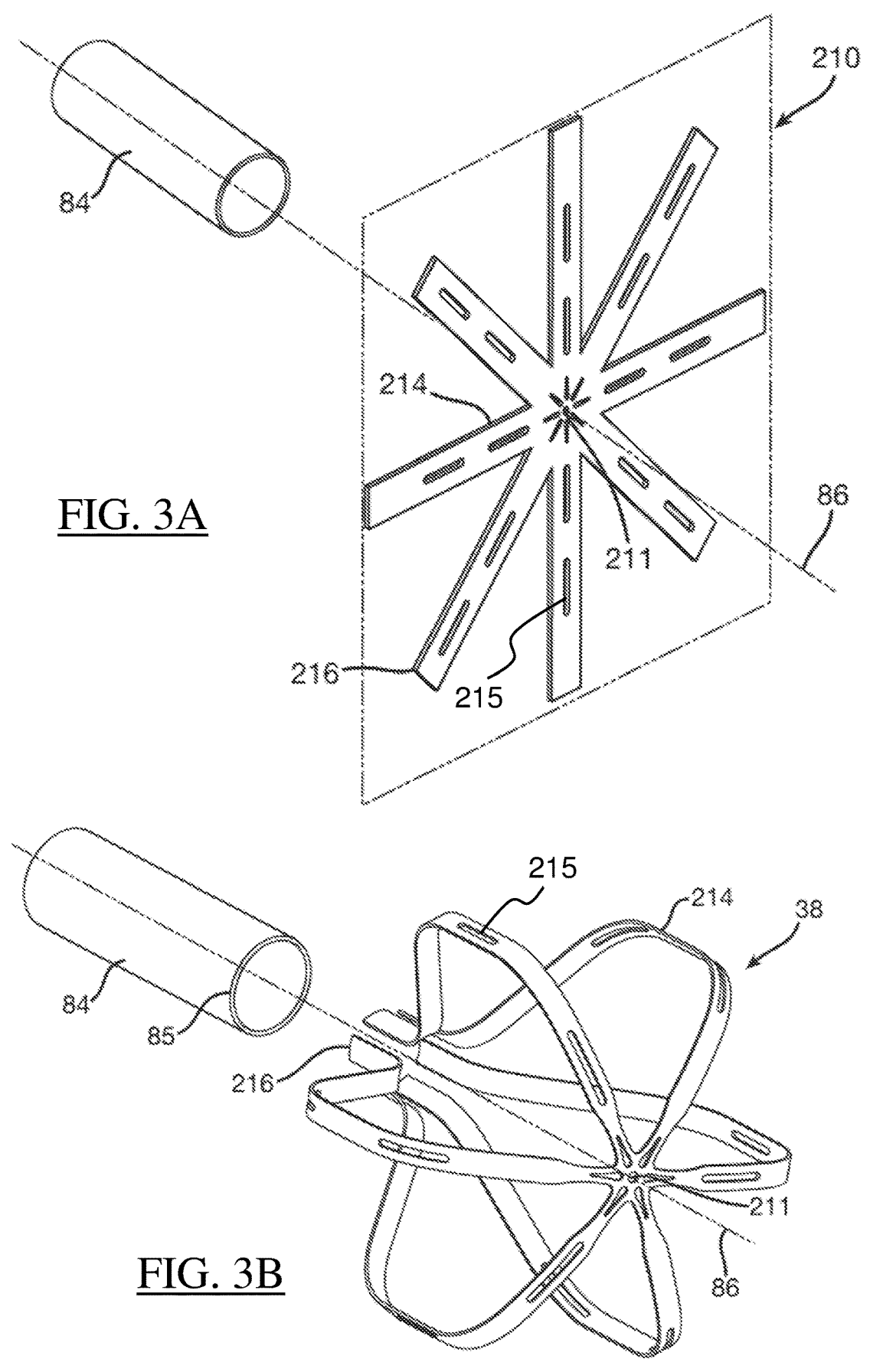

FIGS. 3A and 3B are schematic pictorial illustrations showing exploded views of a tubular shaft 84 and spines 214 of the basket assembly 38 to provide one example of how the spines 214 can be assembled together with the tubular shaft 84, in accordance with an embodiment of the present invention. As shown in FIG. 3A, the spines 214 can form a spine assembly 210. The spines 214 can be formed from a single sheet of planar material to form a generally star shape. In other words, the spines 214 can be formed from the single sheet of planar material such that the spines 214 converge toward a central intersection 211. The intersection 211 can be a solid piece of material or include one or more apertures.

The spines 214 can be folded or otherwise bent such that a proximal end 216 of the spines 214 can be inserted into the distal end 85 of the tubular shaft 84 as shown in FIG. 3B. Although not shown in FIGS. 3A and 3B, it will be appreciated that the electrodes 40 can be attached to the spines 214 before the spines are inserted into the tubular shaft 84 to form the basket assembly 38. As stated previously, the spines 214 can include a flexible, resilient material (e.g., a shape-memory alloy such as nickel-titanium, also known as Nitinol) that can enable the basket assembly 38 to transition from its collapsed form (as shown in FIG. 2B) to its expanded form (as shown in FIG. 2A) when the basket assembly 38 is deployed from the insertion tube 30.

The spines 214 can each define an aperture 215 that can be sized and positioned to receive a locking stub 80 of the electrode 40 as will be described in greater detail herein. By receiving the locking stub 80, the aperture 215 can help to prevent the electrode 40 from sliding proximally or distally along the length of the spine 214. In other words, the aperture 215 can help to secure the electrode 40 to the spine 214 when the locking stub 80 extends through the aperture 215, without requiring a weld, a fastener, adhesive, or other fastening devices or methods. As a non-limiting example, the spines 214 can include at least two apertures 215 positioned on a length of the spine 214 between a proximal end of the spine 214 and a distal end of the spine 214. In this way, the basket assembly 38 can have at least two electrodes 40 along each length of spine 214 extending between the proximal end to the distal end of the basket assembly 38 such that the basket assembly 38 can have a total of twelve electrodes.

As will be appreciated by one skilled in the art with the benefit of this disclosure, the basket assembly 38 shown in FIGS. 2A-3B having spines 214 formed from a single sheet of planar material and converging at a central intersection is offered merely for illustrative purposes and the disclosed technology can be applicable to other configurations of basket assemblies 38. For example, the disclosed technology can be applicable to basket assemblies 38 formed from a single spine 214 or multiple spines 214 with each spine 214 being attached at both ends. In other examples, the basket assembly 38 can include a central hub connecting the multiple spines 214 together at a distal end 94 of the basket assembly 38. In yet other examples, the basket assembly 38 can include a single spine 214 configured to form a spiral, multiple spines 214 configured to form a spiral, multiple spines 214 configured to form a tripod or multiple tripods, or any other shape of basket assembly 38. As well, the spine assembly 210 can be formed by laser cutting a cylindrical hollow stock material whereby the laser is mounted for rotation about the longitudinal axis (and translation thereto) of the cylindrical stock while cutting. Thus, although FIGS. 2A-3B illustrate a specific configuration of basket assembly 38, the disclosed technology should not be construed as so limited.

Figure 4A:
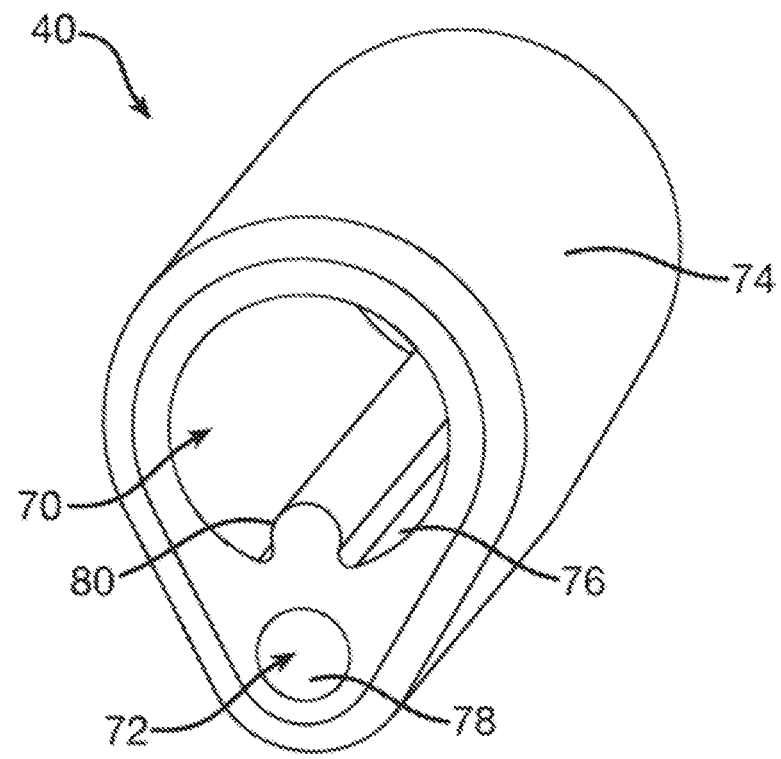
Figure 4B:
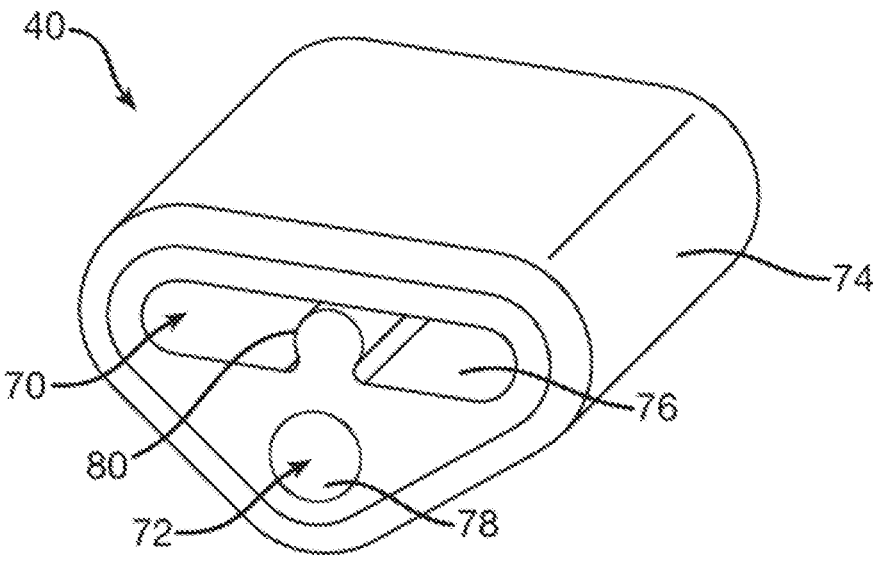
FIG. 4B is a schematic pictorial illustration showing a front perspective view of an electrode after being crimped, in accordance with an embodiment of the present invention.
Figure 5A:
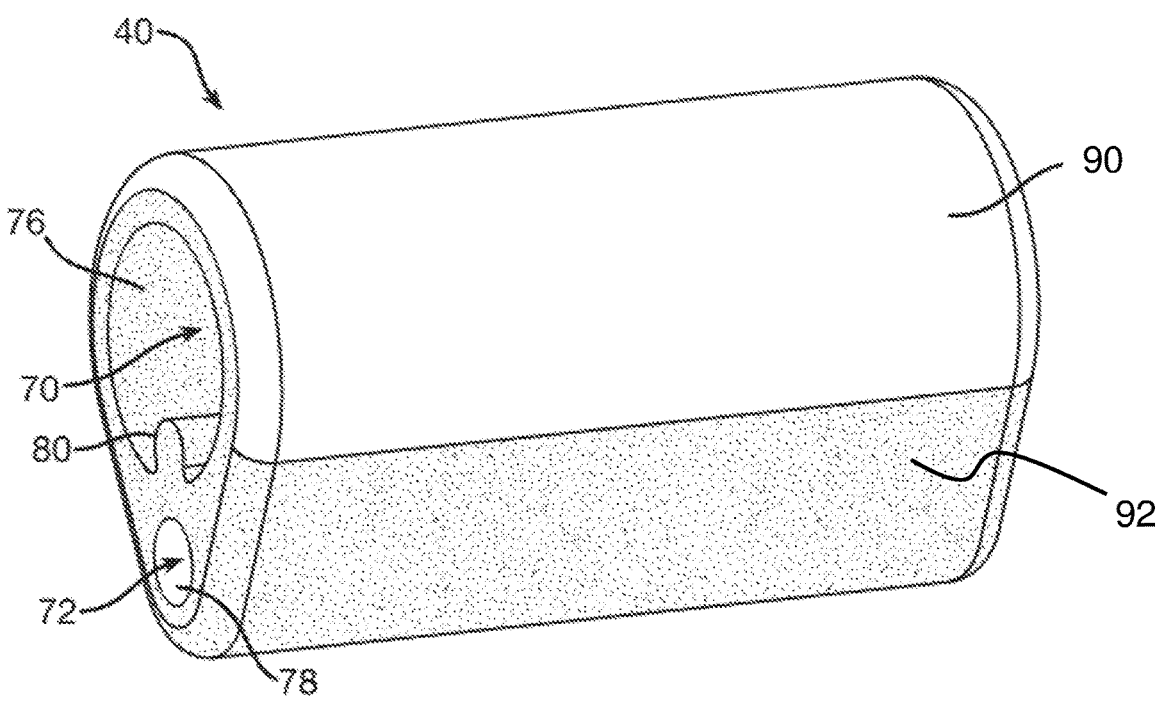
Figure 5B:
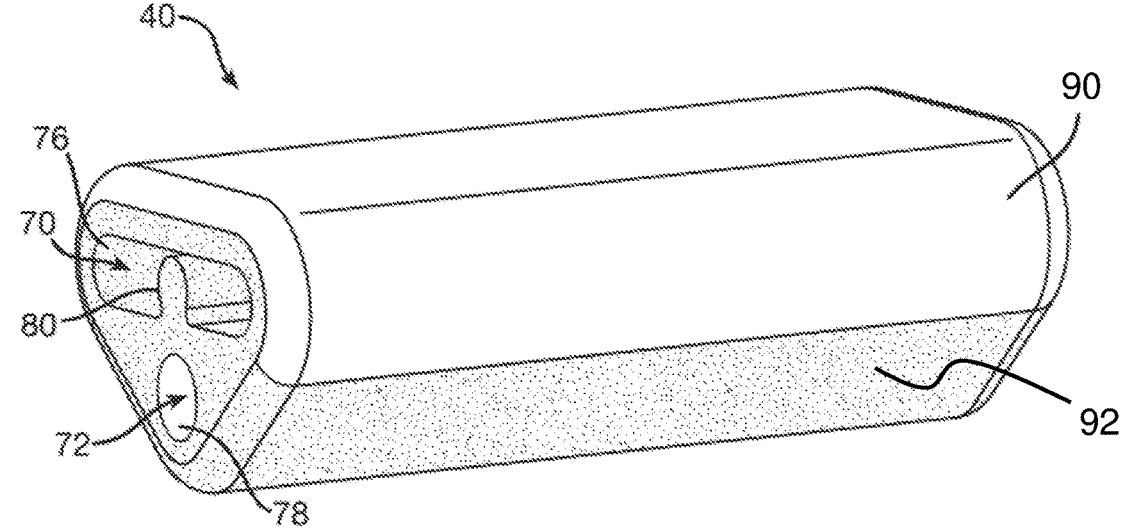
FIG. 5B is a schematic pictorial illustration showing a side perspective view of an electrode after being crimped, in accordance with an embodiment of the present invention.

FIG. 4A is a schematic pictorial illustration showing a front perspective view of an electrode 40 before being crimped while FIG. 4B is a schematic pictorial illustration showing a front perspective view of an electrode 40 after being crimped, in accordance with an embodiment of the present invention. Similarly, FIG. 5A is a schematic pictorial illustration showing a side perspective view of an electrode 40 before being crimped while FIG. 5B is a schematic pictorial illustration showing a side perspective view of an electrode 40 after being crimped, in accordance with an embodiment of the present invention. As shown in FIGS. 4A-5B, the electrode 40 can have an elongated body that has a cross sectional shape that extends along the length of the electrode 40. The electrode 40 can be made from a malleable and conductive material such as gold, platinum, and palladium (and their respective alloys) as described previously. As will be appreciated, by forming the electrode 40 from a malleable material, the electrode 40 can be crimped or otherwise plastically deformed to transition from a first shape (i.e., FIGS. 4A and 5A) that is uncrimped to a second shape (i.e., FIGS. 4B and 5B) that is crimped. As will be described in greater detail herein, the electrode 40 can be crimped around a spine 214 to secure the electrode 40 to the spine 214 without requiring solder, weld, or adhesives.

Figure 6A:
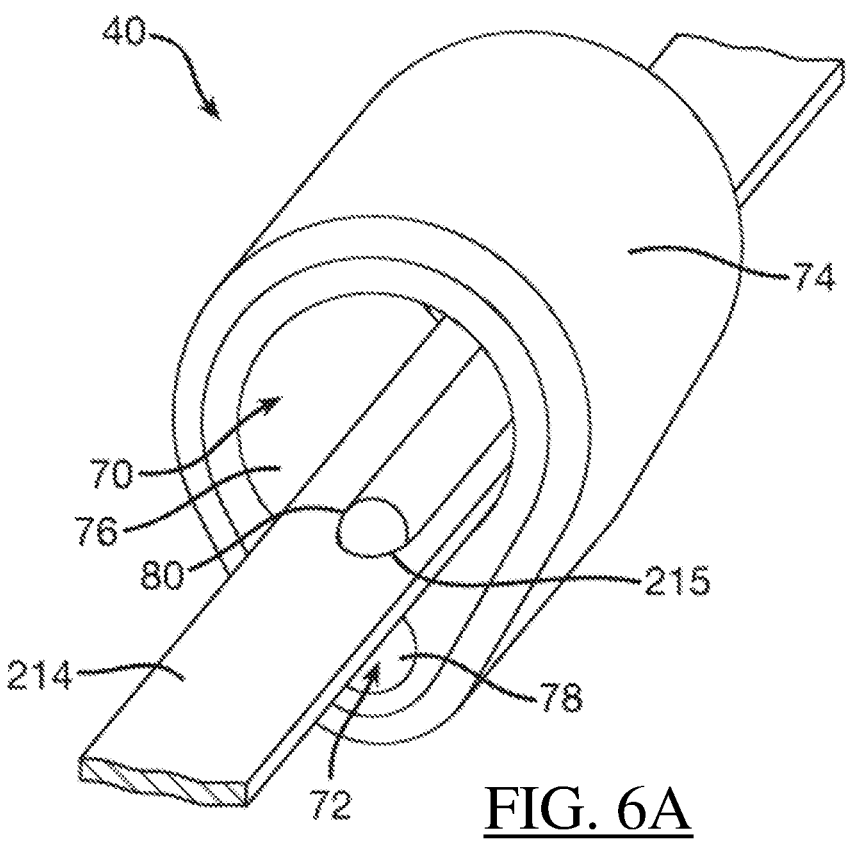

The electrode 40 can define a first lumen 70 and a second lumen 72 which both extend through an elongated body of the electrode 40 from a first end to a second end of the electrode 40. The electrode 40 can have an outer surface 74 facing outwardly from the electrode 40, a first inner surface 76 facing inwardly toward the electrode 40 where the first lumen 70 is formed through the electrode 40, and a second inner surface 78 facing inwardly toward the electrode 40 where the second lumen 72 is formed through the electrode. The first lumen 70 can be sized and configured to receive a spine 214, as shown in FIG. 6A, such that the spine 214 can pass through the first lumen 70. Although not shown, the second lumen 72 can be sized to receive a wire of the medical probe 22 such that the electrode 40 can be attached to the wire. The wire can be electrically insulated from the spine 214. In some examples, the first lumen 70 and/or the second lumen 72 can each pass through the electrode 40 in a generally longitudinal direction of the electrode 40. In other examples, the first lumen 70 and/or the second lumen 72 can pass through the electrode 40 in a generally transverse direction of the electrode 40. Furthermore, the first lumen 70 and/or the second lumen 72 can be positioned in the electrode 40 nearer a bottom surface, nearer at top surface, or nearer a middle of the electrode 40 depending on the particular configuration.

By including a first lumen 70 that is sized to receive the spine 214 of the medical probe 22, the disclosed technology can ensure the electrodes 40 are secured to the spines 214 and prevented from breaking free. Thus, even if the electrodes 40 become dislodged, the electrodes 40 will remain attached to the spines 214 by nature of the strut 430 passing through the first lumen 70.

The electrode 40 can further include a locking stub 80 that can extend inwardly into the first lumen 70. The locking stub 80 can extend longitudinally along the length of the electrode 40 from a first end of the electrode 40 to a second end of the electrode 40. The locking stub 80 can be sized to extend at least partially through an aperture 215 of the spines 214 when the electrode 40 is coupled to the spine 214.

Figure 6B:
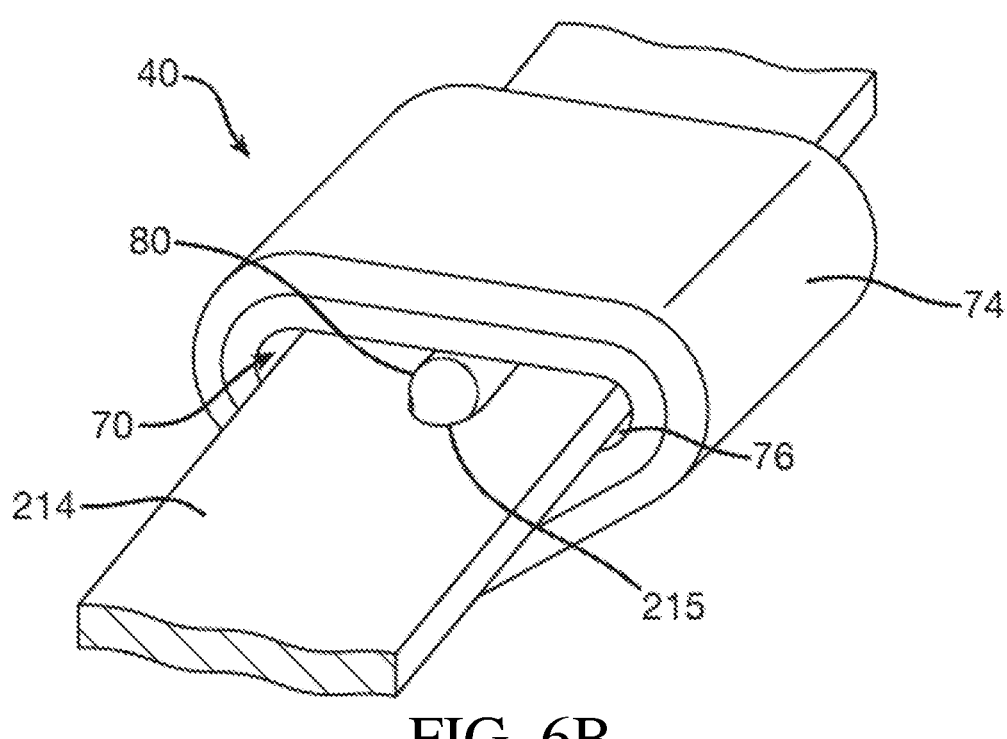
FIG. 6B is a schematic pictorial illustration showing a front perspective view of an electrode and a spine after the electrode is crimped to the spine, in accordance with an embodiment of the present invention.

As illustrated in FIGS. 4A-6B, the electrode 40 can be crimped from a first shape (i.e., as illustrated in FIGS. 4A, 5A, and 6A) to a second shape (i.e., as illustrated in FIGS. 4B, 5B, and 6B). For example, the electrodes 40 can be crimped toward a longitudinal axis of the elongated body of the electrode 40 and have a substantially rounded outer surface 74 prior to being crimped and a substantially flat outer surface 74 after being crimped. The electrodes 40 can be crimped by using a tool to press the electrode 40 until the electrode 40 plastically deforms from the first shape to the second shape. As illustrated in FIGS. 6A and 6B, a spine 214 can be inserted into the electrode 40 and an aperture 215 of the spine 214 can be aligned with the locking stub 80 of the electrode 40. Once the locking stub 80 is aligned with the aperture 215, the electrode 40 can be crimped until a distance between the locking stub 80 and the first lumen inner surface 76 is reduced and the spine 214 is secured in place. In other words, the spine 214 can be inserted into the first lumen 70 and then the electrode 40 can be crimped until electrode 40 is tightly secured around the spine 214. When the electrode 40 is crimped around the spine 214, the locking stub 80 can extend through the aperture 215 of the spine 214 and the electrode 40 can be prevented from moving proximally or distally along the length of the spine 214. Stated otherwise, once the electrode 40 is crimped to spine 40, the locking stub 80 can contact an inner surface of the aperture 215 of the spine 214 and the first lumen inner surface 76 can contact the spine 214 such that the spine 214 cannot be removed from the electrode 40 without deforming the electrode 40. In some examples, the locking stub 80 can form an interference fit with the spine 214 at the aperture 215 to secure the electrode 40 in place.

Figures 7A, 7B, 7C:
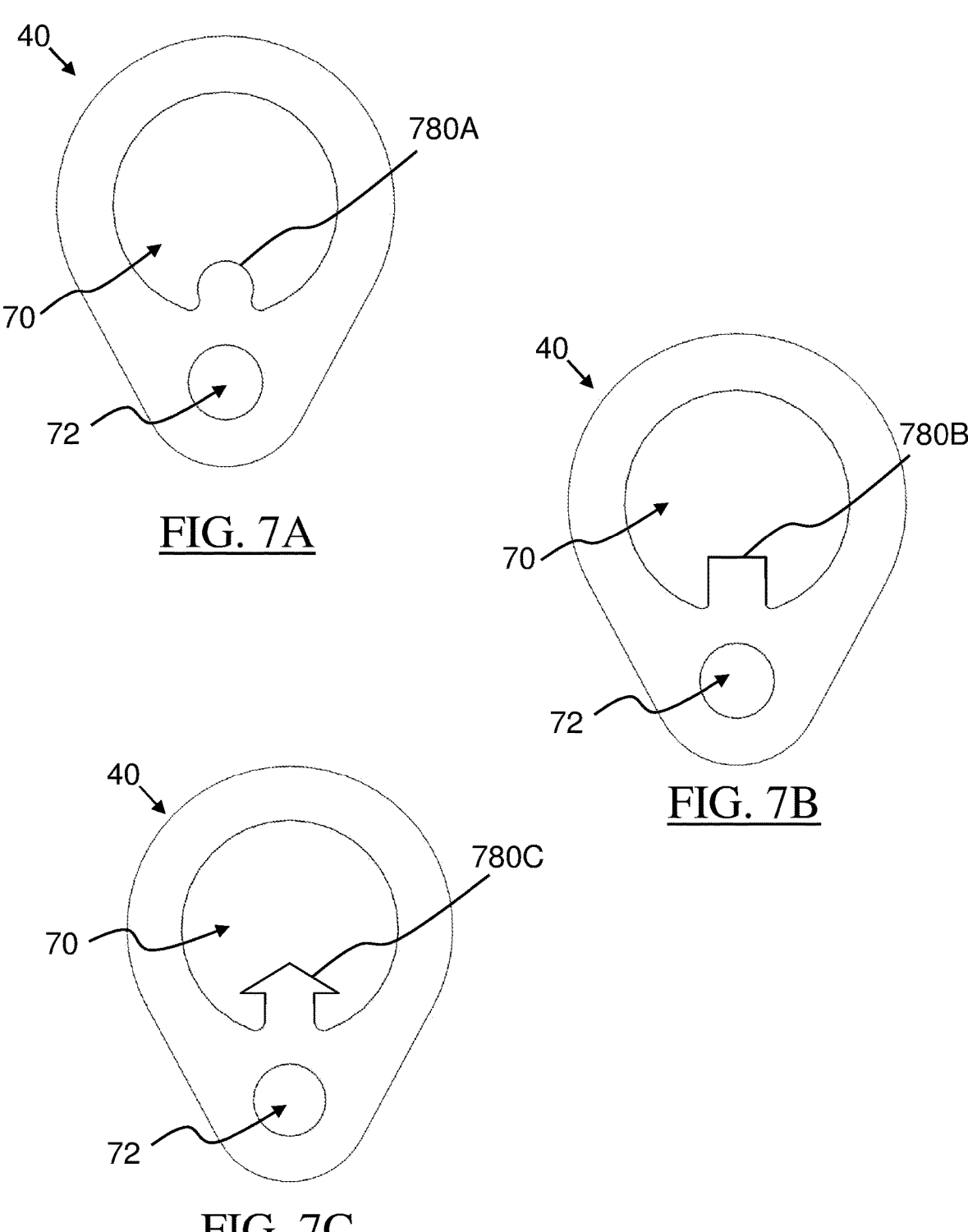
FIGS. 7A-7C illustrate side views of electrodes, in accordance with embodiments of the present invention.

FIGS. 7A-7C illustrate side views of electrodes 40 having locking stubs 780A-780C of different shapes. As shown in FIG. 7A, a locking stub 780A can comprise a generally rounded or circular cross section. Alternatively, as shown in FIG. 7B, a locking stub 780B can comprise a generally rectangular cross section or, as shown in FIG. 7C, a locking stub 780C can comprise at least a portion that has a generally triangular shape. As will be appreciated, a generally rounded locking stub 780A can help to permit the locking stub 780A to slide into the aperture 215 of the spine 214 and form an interference fit with the spine 215. Alternatively, a locking stub 780B having a generally rectangular shape may be able to form a tighter interference fit. Furthermore, a locking stub 780C having a generally triangular shape may be able to lock the spine 214 onto the locking stub 80 with the triangular shape to further secure the electrode 40 to the spine 214. As will be appreciated, FIGS. 7A-7C are offered for explanatory purposes and the disclosed technology should not limited to the specific examples of locking stubs 780A-780C illustrated and described herein. For example, the locking stub 80 can include a generally trapezoidal, pentagonal, hexagonal, octagonal, elliptical, cross, curved, or other suitable shape. Furthermore, the locking stub 80 can have a changing cross section along the length of the locking stub 80 from one end of the locking stub 80 to another end of the locking stub 80. For example, the locking stub 80 can have a thicker cross section at either end of the locking stub 80 or a thicker cross section at the middle of the locking stub 80. Furthermore, although described as extending from one side of the electrode 40 to a second side of the electrode 40, the locking stub 80 can extend less than the full length of the electrode 40 or may have a portion removed between the first end and second end (e.g., the locking stub 80 can have portions of material at either end of the electrode 40 with no material at the middle of the electrode 40). Further still, although a single locking stub 80 is shown and described herein, the electrode 40 can include more than one locking stub 80 and the locking stub 80 can extend into the first lumen 70 from a portion of the first lumen 70 other than the lower portion of the lumen 70 (e.g., an upper portion of the lumen 70). Accordingly, the disclosed technology should not be construed as limited to the particular configurations shown and described herein.

Returning now to FIGS. 5A and 5B, the electrode 40 can include a conductive portion 90 and an insulative portion 92. The conductive portion 90 can be configured to permit electricity to pass therethrough (i.e., for ablation or mapping of the cardiac tissue) and can face generally outward from the basket assembly 80 to face cardiac tissue when in use. The insulative portion 92, on the other hand, can be configured to prevent electricity from passing therethrough to help electrically isolate the spine 214 from the electrode 40. In this way, the insulative portion 92 can prevent a short circuit from forming between the electrode 40 and the spine 214. Furthermore, the insulative portion 92 can direct/focus current during pulsed field ablation. Alternatively, or in addition, the spine 214 can be made from an insulative material or have an insulative coating or sleeve added thereto to electrically isolate the electrode 40 from the spine 214. As yet another example, an electrically insulating material can be placed between the electrode 40 and the spine 214 to electrically isolate the electrode 40 from the spine 214.

Figure 8:
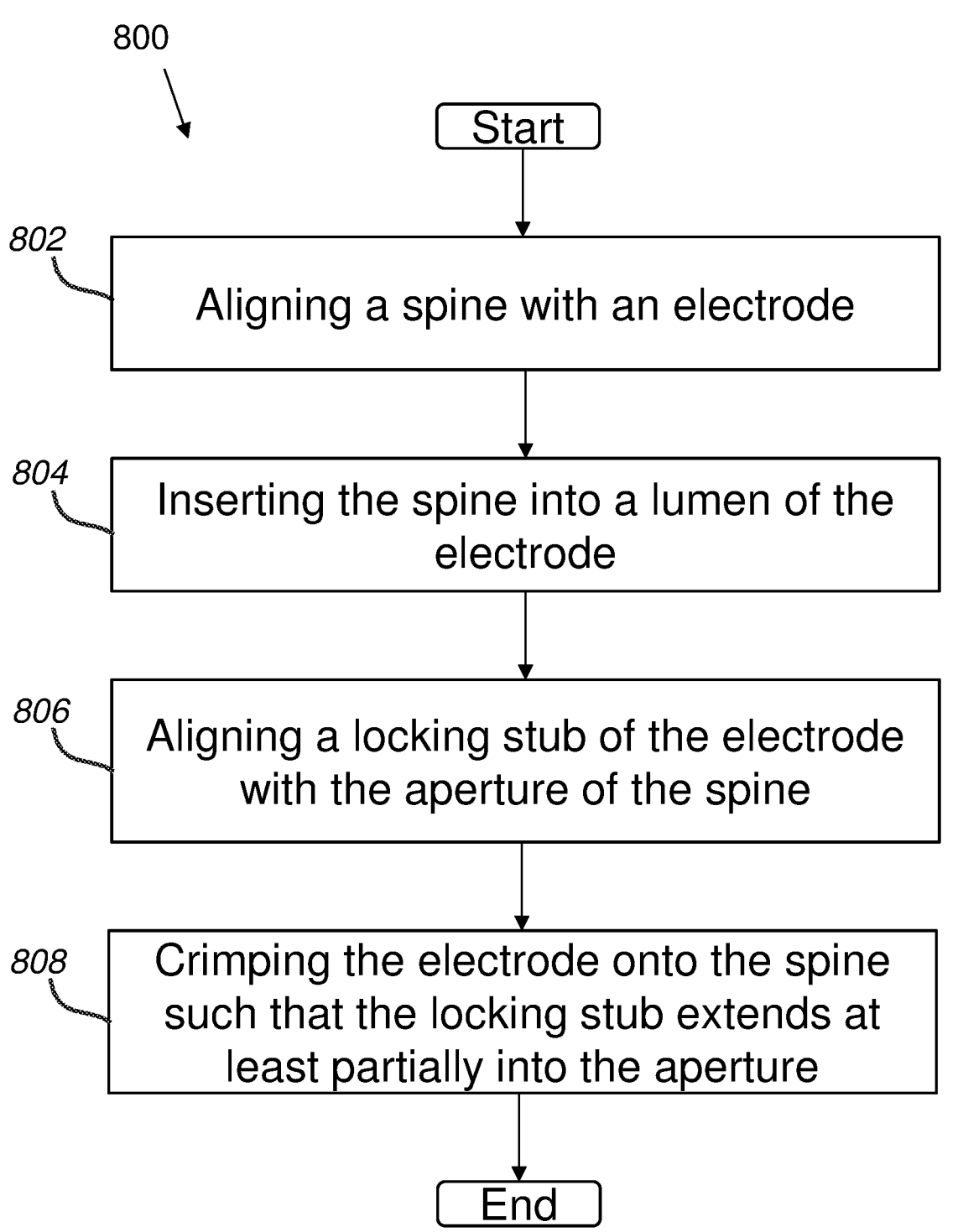
FIG. 8 is a flowchart illustrating a method of constructing a medical probe, in accordance with embodiments of the present disclosure.

FIG. 8 is a flowchart illustrating a method 800 of constructing a medical probe 22, in accordance with embodiments of the present disclosure. The method 800 can include aligning 802 a spine (i.e., spine 214) with an electrode (i.e., electrode 40). Aligning 802 the spine with the electrode, for example, can include aligning the lumen of the electrode (i.e., first lumen 70) with the longitudinal axis of the spine. The method 800 can include inserting 804 the spine into a lumen of the electrode and aligning 806 a locking stub (i.e., locking stub 80) with the aperture (i.e., aperture 215) of the spine. The method can further include crimping 808 the electrode onto the spine such that the locking stub extends at least partially into the aperture to secure the electrode to the spine. Crimping 808 the electrode onto the spine can include using a handheld crimp tool, an electrical crimp tool, a hydraulic crimp tool, a pneumatic crimp tool, or other suitable crimping tool for the application.

As will be appreciated by one skilled in the art, the method 800 can include any of the various features of the disclosed technology described herein and can be varied depending on the particular configuration. For example, the method 800 can further include inserting a wire into the second lumen 72 and electrically connecting the wire to the electrode 40. As another example, the method 800 can include placing an electrically insulative material between the spine 214 and the electrode 40. Furthermore, the method 800 can be repeated as many times as necessary to attach the appropriate number of electrodes 40 to the spine 214 for the particular application.

The disclosed technology described herein can be further understood according to the following clauses:

Clause 1: An electrode for a medical probe, the electrode comprising: an elongated body, at least a portion of the elongated body being electrically conductive, the elongated body defining a lumen extending through the elongated body along a longitudinal axis of the elongated body; and a locking stub extending at least partially into the lumen so that the locking stub is locked to a member inserted into the lumen.

Clause 2: The electrode of clause 1, the electrode configured to be crimped towards the longitudinal axis.

Clause 3: The electrode of clause 2 further comprising a substantially rounded outer surface prior to being crimped and a substantially flat outer surface after being crimped.

Clause 4: The electrode according to any of clauses 1-3, the locking stub having a substantially rounded cross section.

Clause 5: The electrode according to any of clauses 1-3, the locking stub having a substantially rectangular cross section.

Clause 6: The electrode according to any of clauses 1-3, at least a portion of the locking stub comprising a substantially triangular cross section.

Clause 7: The electrode according to any of clauses 1-6, wherein the locking stub extends a length of the elongated body.

Clause 8: The electrode according to any of clauses 1-7, the elongated body further comprising an insulative material configured to electrically isolate the electrode from the member inserted into the lumen.

Clause 9: The electrode according to any of clauses 1-8, the lumen being a first lumen, wherein the elongated body further defines a second lumen configured to receive a wire.

Clause 10: The electrode according to clause 9, wherein the wire is electrically coupled to the electrode.

Clause 11: A medical probe, comprising: a tubular shaft having a proximal end and a distal end, the tubular shaft extending along a longitudinal axis; and an expandable basket assembly coupled to the distal end of the tubular shaft, the expandable basket assembly comprising: a plurality of electrodes, each electrode of the plurality of electrodes defining a lumen extending therethrough and a locking stub extending at least partially into the lumen; and a plurality of spines extending along the longitudinal axis and configured to bow radially outward from the longitudinal axis when the expandable basket assembly is transitioned from a collapsed form to an expanded form, each spine of the plurality of spines passing through a lumen of an electrode of the plurality of electrodes, each spine of the plurality of spines defining an aperture extending therethrough from a first side of the spine to a second side of the spine, the aperture configured to receive the locking stub of the electrode such that when the electrode is mechanically coupled to the spine, the locking stub extends through the aperture preventing the electrode from sliding distally or proximally along the spine.

Clause 12: The medical probe according to clause 11, each electrode of the plurality of electrodes being configured to be crimped to the spine.

Clause 13: The medical probe according to clause 12, each electrode of the plurality of electrodes having a substantially rounded outer surface prior to being crimped to the spine and having a substantially flat outer surface after being crimped to the spine.

Clause 14: The medical probe according to any of clauses 11-13, the locking stub having a substantially rounded cross section.

Clause 15: The medical probe according to any of clauses 11-13, the locking stub having a substantially rectangular cross section.

Clause 16: The medical probe according to any of clauses 11-13, wherein at least a portion of the locking stub comprises a substantially triangular cross section.

Clause 17: The medical probe according to any of clauses 11-16, each electrode of the plurality of electrodes further comprising an insulative material configured to electrically isolate the electrode from the spine.

Clause 18: The medical probe according to any of clauses 11-16, each spine of the plurality of spines further comprising an insulative material configured to electrically isolate the spine from the electrode.

Clause 19: The medical probe according to any of clauses 11-18, wherein the expandable basket assembly further comprises an insulative material disposed between the electrode and the spine to electrically isolate the electrode from the spine.

Clause 20: The medical probe according to any of clauses 11-19, the lumen of each electrode of the plurality of electrodes being a first lumen, each electrode of the plurality of electrodes further defining a second lumen configured to receive a wire of the medical probe.

Clause 21: The medical probe according to clause 20, wherein the wire is electrically coupled to the electrode.

Clause 22: The medical probe according to clause 21, wherein the wire is insulated from the spine.

Clause 23: The medical probe according to any of clauses 11-21, wherein each spine of the plurality of spines comprises a first electrode and a second electrode mechanically coupled to the spine, and wherein each spine defines a first aperture configured to receive a locking stub of the first electrode and a second aperture configured to receive a locking stub of the second electrode, the first aperture and the second aperture both being configured to prevent the first and second electrodes from sliding proximally or distally along a length of the spine when the first and second electrodes are mechanically coupled to the spine, respectively.

Clause 24: The medical probe according to any one of clauses 11-22, wherein an interface between the locking stub of the electrode and the spine at the aperture comprises an interference fitting.

Clause 25: The medical probe according to any of clauses 11-24, wherein the spine comprises a material selected from a group consisting of nitinol, cobalt chromium, stainless steel, titanium and combinations thereof.

Clause 26: The medical probe according to any of clauses 11-24, wherein the spine comprises a polymer material.

Clause 27: The medical probe according to any of clauses 11-26, wherein the plurality of electrodes is configured to deliver electrical pulses for irreversible electroporation, the pulses having a peak voltage of at least 900 volts (V).

Clause 28: The medical probe according to any of clauses 11-26, wherein the plurality of electrodes is configured for mapping electrophysiological characteristics of cardiac tissue.

Clause 29: The medical probe according to any of clauses 11-28, further comprising spray ports configured to deliver an irrigation fluid to the plurality of electrodes.

Clause 30: A method of constructing a medical probe, the method comprising: aligning a spine of an expandable basket assembly with an electrode of the expandable basket assembly, the spine comprising a proximal end, a distal end, and defining an aperture extending therethrough; inserting the spine into a lumen of the electrode; aligning a locking stub of the electrode with the aperture; and crimping the electrode onto the spine such that the locking stub extends at least partially into the aperture to prevent the electrode from sliding proximally or distally along the spine.

Clause 31: The method according to clause 30, the electrode having a substantially rounded outer surface prior to being crimped to the spine and having a substantially flat outer surface after being crimped to the spine.

Clause 32: The method according to any of clauses 30-31, the locking stub having a substantially rounded cross section.

Clause 33: The method according to any of clauses 30-31, the locking stub having a substantially rectangular cross section.

Clause 34: The method according to any of clauses 30-31, wherein at least a portion of the locking stub comprises a substantially triangular cross section.

Clause 35: The method according to any of clauses 30-34, the electrode further comprising an insulative material configured to electrically isolate the electrode from the spine.

Clause 36: The method according to any of clauses 30-34, the spine further comprising an insulative material configured to electrically isolate the spine from the electrode.

Clause 37: The method according to any of clauses 30-36, wherein the expandable basket assembly further comprises an insulative material disposed between the electrode and the spine to electrically isolate the electrode from the spine.

Clause 38: The method according to any of clauses 30-37, wherein the lumen comprises a first lumen, the method further comprising: aligning a wire of the medical probe with a second lumen of the electrode; inserting the wire into the second lumen; and coupling the wire to the electrode such that the wire is in electrical communication with the electrode.

Clause 39: The method according to clause 38, wherein the wire is insulated from the spine.

Clause 40: The method according to any of clauses 30-39, wherein an interface between the locking stub of the electrode and the spine at the aperture comprises an interference fitting.

Clause 41: The method according to any of clauses 30-40, wherein the spine comprises a material selected from a group consisting of nitinol, cobalt chromium, stainless steel, titanium.

Clause 42: The method according to any of clauses 30-41, wherein the spine comprises a polymer material.

Clause 43: The method according to any of clauses 30-42, wherein the aperture of the spine is a first aperture, the spine further defining a second aperture, the method further comprising: aligning the spine with a second electrode of the expandable basket assembly; inserting the spine into a lumen of the second electrode; aligning a locking stub of the second electrode with the second aperture; and crimping the second electrode onto the spine such that the locking stub extends at least partially into the second aperture to prevent the second electrode from sliding proximally or distally along the spine.

The embodiments described above are cited by way of example, and the present invention is not limited by what has been particularly shown and described hereinabove. Rather, the scope of the invention includes both combinations and sub combinations of the various features described hereinabove, as well as variations and modifications thereof which would occur to persons skilled in the art upon reading the foregoing description and which are not disclosed in the prior art.

What is claimed is:

1. A medical probe, comprising:
a tubular shaft having a proximal end and a distal end, the tubular shaft extending along a longitudinal axis; and
an expandable basket assembly coupled to the distal end of the tubular shaft, the expandable basket assembly comprising:
a plurality of electrodes, each electrode of the plurality of electrodes defining a lumen extending therethrough and a locking stub extending at least partially into the lumen; and
a plurality of spines extending along the longitudinal axis and configured to bow radially outward from the longitudinal axis when the expandable basket assembly is transitioned from a collapsed form to an expanded form, each spine of the plurality of spines passing through the lumen of a respective electrode of the plurality of electrodes, each spine of the plurality of spines defining an aperture extending therethrough from a first side of the spine to a second side of the spine, the aperture configured to receive the locking stub of the respective electrode of the plurality of electrodes such that when the respective electrode of the plurality of electrodes is mechanically coupled to the spine, the locking stub extends through the aperture preventing the respective electrode of the plurality of electrodes from sliding distally or proximally along the spine.

2. The medical probe according to claim 1, each electrode of the plurality of electrodes being configured to be crimped to the spine.

3. The medical probe according to claim 2, each electrode of the plurality of electrodes having a substantially rounded outer surface prior to being crimped to the spine and having a substantially flat outer surface after being crimped to the spine.

4. The medical probe according claim 1, each electrode of the plurality of electrodes further comprising an insulative material configured to electrically isolate each electrode of the plurality of electrodes from the spine.

5. The medical probe according to claim 1, each spine of the plurality of spines further comprising an insulative material configured to electrically isolate the spine from each electrode of the plurality of electrodes.

6. The medical probe according to claim 1, wherein the respective electrode mechanically coupled to each spine of the plurality of spines comprises a first respective electrode, the aperture of each spine of the plurality of spines comprises a first respective aperture, and each spine of the plurality of spines comprises and a second respective electrode of the plurality of electrodes, and
wherein each spine defines a second respective aperture configured to receive the locking stub of the second respective electrode of the plurality of electrodes, the first respective aperture and the second respective aperture both being configured to prevent the first and second respective electrodes of the plurality of electrodes from sliding proximally or distally along a length of the spine when the first and second respective electrodes of the plurality of electrodes are mechanically coupled to the spine.

7. The medical probe of claim 1, wherein an interface between the locking stub of the respective electrode and the spine at the aperture comprises an interference fitting.

8. The medical probe according to claim 1, wherein the plurality of electrodes are electrically connected to an ablation module and configured to deliver electrical pulses for irreversible electroporation, the pulses having a peak voltage of at least 900 volts (V).

9. A method of constructing a medical probe, the method comprising:
aligning a spine of an expandable basket assembly with an electrode of the expandable basket assembly,
the spine comprising a proximal end, a distal end, and defining an aperture extending therethrough from a first side of the spine to a second side of the spine, the spine extending along a longitudinal axis and configured to bow radially outward from the longitudinal axis when the expandable basket assembly is transitioned from a collapsed form to an expanded form, and
the electrode defining a lumen extending therethrough and a locking stub extending at least partially into the lumen;
inserting the spine into the lumen of the electrode;
aligning the locking stub of the electrode with the aperture; and
crimping the electrode onto the spine such that the locking stub extends at least partially into the aperture to mechanically couple the electrode to the spine and to prevent the electrode from sliding proximally or distally along the spine.

10. The method according to claim 9, wherein the lumen comprises a first lumen, the method further comprising:
aligning a wire of the medical probe with a second lumen of the electrode;
inserting the wire into the second lumen; and
coupling the wire to the electrode such that the wire is in electrical communication with the electrode.

* * * * *